US008809262B2

(12) United States Patent
Beuerman et al.

(10) Patent No.: US 8,809,262 B2
(45) Date of Patent: Aug. 19, 2014

(54) MULTIMERIC FORMS OF ANTIMICROBIAL PEPTIDES

(75) Inventors: Roger W. Beuerman, Singapore (SG); Shouping Liu, Singapore (SG); Jing Li, Singapore (SG); Lei Zhou, Singapore (SG); Chandra Shekhar Verma, Singapore (SG); Donald Tan, Singapore (SG)

(73) Assignees: Singapore Health Service Pte Ltd., Singapore (SG); Agency for Science, Technology and Research, Singapore (SG)

( * ) Notice: Subject to any disclaimer, the term of this patent is extended or adjusted under 35 U.S.C. 154(b) by 273 days.

(21) Appl. No.: 12/988,994

(22) PCT Filed: Apr. 21, 2009

(86) PCT No.: PCT/SG2009/000144
§ 371 (c)(1), (2), (4) Date: Oct. 21, 2010

(87) PCT Pub. No.: WO2009/131548
PCT Pub. Date: Oct. 29, 2009

(65) Prior Publication Data
US 2011/0039760 A1    Feb. 17, 2011

Related U.S. Application Data

(60) Provisional application No. 61/046,584, filed on Apr. 21, 2008.

(51) Int. Cl.
*A61K 38/00* (2006.01)
*C07K 1/00* (2006.01)

(52) U.S. Cl.
USPC ............ 514/2.3; 514/2.4; 514/21.3; 530/324; 530/328; 530/331; 530/334

(58) Field of Classification Search
None
See application file for complete search history.

(56) References Cited

U.S. PATENT DOCUMENTS

| | | | | |
|---|---|---|---|---|
| 5,057,520 A | * | 10/1991 | Chu et al. ...................... | 514/300 |
| 5,639,594 A | * | 6/1997 | Wang et al. ...................... | 435/5 |
| 5,919,761 A | * | 7/1999 | Wakefield et al. ............ | 514/13.7 |
| 7,531,505 B2 | * | 5/2009 | Hamilton et al. ............... | 514/1.1 |

FOREIGN PATENT DOCUMENTS

| | | |
|---|---|---|
| JP | 2006-508720 A | 3/2003 |
| WO | WO 2007/007116 | 1/2007 |
| WO | WO 2007/025178 | 3/2007 |
| WO | WO 2007/126392 | 11/2007 |

OTHER PUBLICATIONS

Hoover et al. Antimicrobial Agents and Chemotherapy, 2003.*
Schibil et al. J Biol Chem 2002.*
Funderburg PNAS 104:18631-18635, 2007.*
Campopiano, D. J., et al. "Structure-Activity Relationships in Defensin Dimers" The Journal of Biologicals Chemistry, vol. 279, No. 47, Issue of Nov. 19, 2004, pp. 48671-48679.
Hoover, D.M., et al. "The Structure of Human β-Defensin-2 Shows Evidence of Higher Order Oligomerization" The Journal of Biological Chemistry, vol. 275, No. 42, Issue of Oct. 20, 2000, pp. 32911-32918.
Schibli D.J., et al. "The Solution Structures of the Human β-Defensins Lead to a Better Understanding of the Potent Bactericidal Activity of HBD3 against *Staphylococcus aureaus*" The Journal of biological Chemistry. vol. 277, No. 10, Issue of Mar. 8, 2002, pp. 8279-8289.
International Search Report, mailed Jul. 9, 2009 in related International application No. PCT/SG2009/000144 filed Apr. 21, 2009.
Written Opinion, mailed Jul. 9, 2009 in related International application No. PCT/SG2009/000144 filed Apr. 21, 2009.
International Preliminary Report on Patentability, mailed Oct. 26, 2010 in related International application No. PCT/SG2009/000144 filed Apr. 21, 2009.
Arnusch, C.J. et al., "Enhanced membrane pore formation by multimeric/oligomeric antimicrobial peptides," Biochemistry Nov. 2007, American Chemical Society, vol. 46, No. 46, pp. 13437-13442.
Liu, Shouping, et al., "Linear analogues of human beta-defensin 3: concepts for design of antimicrobial peptides with reduced cytotoxicity to mammalian cells", Chembiochem—A European Journal of Chemical Biology, vol. 9, No. 6, Apr. 14, 2008, pp. 964-973.
Zhou, L. et al., "The structural parameters for antimicrobial activity, human epithelial cell cytotoxicity and killing mechanism of synthetic monomer and dimer analogues derived from hBD3 C-terminal region", Amino Acides, The Forum for Amino Acid and Protein Research, vol. 40, No. 1, Apr. 17, 2010, pp. 123-133.
Supplementary European Search Report, mailed Jul. 14, 2011 in related European application No. EP 09 73 4345, 3 pages.
Dhople et al., "The human beta-defensin-3, an antibacterial peptide with multiple biological functions," Biochim. Biophys. Acta 1758:1499-1512 (2006).
Liu et al., "Multivalent Antimicrobial Peptides as Therapeutics: Design Principles and Structural Diversities," Int. J. Pept. Res. Ther. 16:199-213 (2010).
Pini et al., "Antimicrobial Activity of Novel Dendrimeric Peptides Obtained by Phage Display Selection and Rational Modification," Antimicrob. Agents Chemother. 49:2665-2672 (2005).
Yang et al., "Effect of dimerization of a β-turn antimicrobial peptide, PST13-RK, on antimicrobial activity and mammalian cell toxicity," Biotechnol. Left. 31:233-237 (2009).

* cited by examiner

*Primary Examiner* — James H Alstrum Acevedo
*Assistant Examiner* — Li Lee
(74) *Attorney, Agent, or Firm* — Cooley LLP

(57) ABSTRACT

The invention relates to multimeric forms of antimicrobial peptides, for example, defensin peptides. The multimeric forms of defensin peptides possesses antimicrobial activity and may be formulated into antimicrobial compositions, pharmaceutical compositions, eyedrop composition, contact lens solution compositions for coating medical devices and the like. The invention also relates to the use of these multimeric forms of peptides, e.g. multimeric forms of defensin peptides for inhibiting and/or reducing the growth of microorganisms in general, including in a host. The invention further relates to a method of preparing multimers of peptides derived from defensins, for example hBD3.

18 Claims, 8 Drawing Sheets

Figure 1

$CH_2(CH_2)_3NH$ – Fmoc
|
Fmoc –NH– CH – COOH        Lys (Fmoc)

RGRKVVRRKK        V2 –monomer $(RGRKVVRR)_2KK$        V2 –dimer

NH2-R(pbf)R(pbf)VVK(boc)R(pbf)GR(pbf)-NH-Lys(Boc)-Wang Resin

NH2-R(pbf)R(pbf)VVK(boc)R(pbf)GR(pbf)-NH-Lys(Boc)-Wang Resin heterotrimer

V2-tetramer

```
                         SEQUENCE LISTING

<160> NUMBER OF SEQ ID NOS: 58

<210> SEQ ID NO 1
<211> LENGTH: 45
<212> TYPE: PRT
<213> ORGANISM: Homo sapiens

<400> SEQUENCE: 1

Gly Ile Ile Asn Thr Leu Gln Lys Tyr Tyr Cys Arg Val Arg Gly Gly
1               5                   10                  15

Arg Cys Ala Val Leu Ser Cys Leu Pro Lys Glu Glu Gln Ile Gly Lys
            20                  25                  30

Cys Ser Thr Arg Gly Arg Lys Cys Cys Arg Arg Lys Lys
        35                  40                  45

<210> SEQ ID NO 2
<211> LENGTH: 45
<212> TYPE: PRT
<213> ORGANISM: Artificial Sequence
<220> FEATURE:
<223> OTHER INFORMATION: hBD3 derived peptide, C replaced with X
<220> FEATURE:
<221> NAME/KEY: MISC_FEATURE
<222> LOCATION: (11)..(41)
<223> OTHER INFORMATION: Xaa comprises any amino acid
<220> FEATURE:
<221> NAME/KEY: MISC_FEATURE
<222> LOCATION: (44)..(45)
<223> OTHER INFORMATION: Xaa comprises any amino acid or may be absent

<400> SEQUENCE: 2

Gly Ile Ile Asn Thr Leu Gln Lys Tyr Tyr Xaa Arg Val Arg Gly Gly
1               5                   10                  15

Arg Xaa Xaa Val Leu Ser Ala Leu Pro Lys Glu Glu Gln Ile Gly Lys
            20                  25                  30

Xaa Ser Thr Arg Gly Arg Lys Xaa Xaa Arg Arg Xaa Xaa
        35                  40                  45

<210> SEQ ID NO 3
<211> LENGTH: 43
<212> TYPE: PRT
<213> ORGANISM: Artificial Sequence
<220> FEATURE:
<223> OTHER INFORMATION: hBD3 fragment excluding terminal KK, C
      residues replaced with X
<220> FEATURE:
<221> NAME/KEY: MISC_FEATURE
<222> LOCATION: (11)..(41)
<223> OTHER INFORMATION: Xaa comprises any amino acid

<400> SEQUENCE: 3

Gly Ile Ile Asn Thr Leu Gln Lys Tyr Tyr Xaa Arg Val Arg Gly Gly
1               5                   10                  15

Arg Xaa Ala Val Leu Ser Xaa Leu Pro Lys Glu Glu Gln Ile Gly Lys
            20                  25                  30

Xaa Ser Thr Arg Gly Arg Lys Xaa Xaa Arg Arg
        35                  40
```

```
<210> SEQ ID NO 4
<211> LENGTH: 38
<212> TYPE: PRT
<213> ORGANISM: Artificial Sequence
<220> FEATURE:
<223> OTHER INFORMATION: hBD3 derived C terminus 38 aa peptide
<220> FEATURE:
<221> NAME/KEY: MISC_FEATURE
<222> LOCATION: (4)..(34)
<223> OTHER INFORMATION: Xaa comprises any amino acid
<220> FEATURE:
<221> NAME/KEY: MISC_FEATURE
<222> LOCATION: (37)..(38)
<223> OTHER INFORMATION: Xaa comprises any amino acid or may be absent

<400> SEQUENCE: 4

Lys Tyr Tyr Xaa Arg Val Arg Gly Gly Arg Xaa Ala Val Leu Ser Xaa
 1               5                  10                  15

Leu Pro Lys Glu Glu Gln Ile Gly Lys Xaa Ser Thr Arg Gly Arg Lys
            20                  25                  30

Xaa Xaa Arg Arg Xaa Xaa
         35

<210> SEQ ID NO 5
<211> LENGTH: 36
<212> TYPE: PRT
<213> ORGANISM: Artificial Sequence
<220> FEATURE:
<223> OTHER INFORMATION: hBD3 derived C terminus 36 aa peptide
<220> FEATURE:
<221> NAME/KEY: MISC_FEATURE
<222> LOCATION: (2)..(32)
<223> OTHER INFORMATION: Xaa comprises any amino acid
<220> FEATURE:
<221> NAME/KEY: MISC_FEATURE
<222> LOCATION: (35)..(36)
<223> OTHER INFORMATION: Xaa comprises any amino acid or may be absent

<400> SEQUENCE: 5

Tyr Xaa Arg Val Arg Gly Gly Arg Xaa Ala Val Leu Ser Xaa Leu Pro
 1               5                  10                  15

Lys Glu Glu Gln Ile Gly Lys Xaa Ser Thr Arg Gly Arg Lys Xaa Xaa
            20                  25                  30

Arg Arg Xaa Xaa
         35

<210> SEQ ID NO 6
<211> LENGTH: 40
<212> TYPE: PRT
<213> ORGANISM: Artificial Sequence
<220> FEATURE:
<223> OTHER INFORMATION: hBD3 derived C terminus 40 aa peptide
<220> FEATURE:
<221> NAME/KEY: MISC_FEATURE
<222> LOCATION: (6)..(36)
<223> OTHER INFORMATION: Xaa comprises any amino acid
<220> FEATURE:
<221> NAME/KEY: MISC_FEATURE
<222> LOCATION: (39)..(40)
<223> OTHER INFORMATION: Xaa comprises any amino acid or may be absent

<400> SEQUENCE: 6

Leu Gln Lys Tyr Tyr Xaa Arg Val Arg Gly Gly Arg Xaa Ala Val Leu
 1               5                  10                  15

Ser Xaa Leu Pro Lys Glu Glu Gln Ile Gly Lys Xaa Ser Thr Arg Gly
            20                  25                  30
```

Arg Lys Xaa Xaa Arg Arg Xaa Xaa
         35                  40

<210> SEQ ID NO 7
<211> LENGTH: 29
<212> TYPE: PRT
<213> ORGANISM: Artificial Sequence
<220> FEATURE:
<223> OTHER INFORMATION: hBD3 derived C terminus 29 aa peptide
<220> FEATURE:
<221> NAME/KEY: MISC_FEATURE
<222> LOCATION: (2)..(25)
<223> OTHER INFORMATION: Xaa comprises any amino acid
<220> FEATURE:
<221> NAME/KEY: MISC_FEATURE
<222> LOCATION: (28)..(29)
<223> OTHER INFORMATION: Xaa comprises any amino acid or may be absent

<400> SEQUENCE: 7

Arg Xaa Ala Val Leu Ser Xaa Leu Pro Lys Glu Glu Gln Ile Gly Lys
1               5                   10                  15

Xaa Ser Thr Arg Gly Arg Lys Xaa Xaa Arg Arg Xaa Xaa
            20                  25

<210> SEQ ID NO 8
<211> LENGTH: 20
<212> TYPE: PRT
<213> ORGANISM: Artificial Sequence
<220> FEATURE:
<223> OTHER INFORMATION: hBD3 derived C terminus 20 aa peptide
<220> FEATURE:
<221> NAME/KEY: MISC_FEATURE
<222> LOCATION: (8)..(16)
<223> OTHER INFORMATION: Xaa comprises any amino acid
<220> FEATURE:
<221> NAME/KEY: MISC_FEATURE
<222> LOCATION: (19)..(20)
<223> OTHER INFORMATION: Xaa comprises any amino acid or may be absent

<400> SEQUENCE: 8

Lys Glu Glu Gln Ile Gly Lys Xaa Ser Thr Arg Gly Arg Lys Xaa Xaa
1               5                   10                  15

Arg Arg Xaa Xaa
            20

<210> SEQ ID NO 9
<211> LENGTH: 14
<212> TYPE: PRT
<213> ORGANISM: Artificial Sequence
<220> FEATURE:
<223> OTHER INFORMATION: hBD3 derived C terminus 14 aa peptide
<220> FEATURE:
<221> NAME/KEY: MISC_FEATURE
<222> LOCATION: (2)..(10)
<223> OTHER INFORMATION: Xaa comprises any amino acid
<220> FEATURE:
<221> NAME/KEY: MISC_FEATURE
<222> LOCATION: (13)..(14)
<223> OTHER INFORMATION: Xaa comprises any amino acid or may be absent

<400> SEQUENCE: 9

Lys Xaa Ser Thr Arg Gly Arg Lys Xaa Xaa Arg Arg Xaa Xaa
1               5                   10

<210> SEQ ID NO 10
<211> LENGTH: 19
<212> TYPE: PRT
<213> ORGANISM: Artificial Sequence
<220> FEATURE:
<223> OTHER INFORMATION: hBD3 derived peptide from aa 8 to 26

-continued

```
<220> FEATURE:
<221> NAME/KEY: MISC_FEATURE
<222> LOCATION: (4)..(16)
<223> OTHER INFORMATION: Xaa comprises any amino acid

<400> SEQUENCE: 10

Lys Tyr Tyr Xaa Arg Val Arg Gly Gly Arg Xaa Ala Val Leu Ser Xaa
1               5                   10                  15

Leu Pro Lys

<210> SEQ ID NO 11
<211> LENGTH: 17
<212> TYPE: PRT
<213> ORGANISM: Artificial Sequence
<220> FEATURE:
<223> OTHER INFORMATION: hBD3 derived N terminus 17 aa peptide
<220> FEATURE:
<221> NAME/KEY: MISC_FEATURE
<222> LOCATION: (11)..(11)
<223> OTHER INFORMATION: Xaa comprises any amino acid

<400> SEQUENCE: 11

Gly Ile Ile Asn Thr Leu Gln Lys Tyr Tyr Xaa Arg Val Arg Gly Gly
1               5                   10                  15

Arg

<210> SEQ ID NO 12
<211> LENGTH: 45
<212> TYPE: PRT
<213> ORGANISM: Artificial Sequence
<220> FEATURE:
<223> OTHER INFORMATION: hBD3 derived peptide, C replaced with W
<220> FEATURE:
<221> NAME/KEY: MISC_FEATURE
<222> LOCATION: (44)..(45)
<223> OTHER INFORMATION: Xaa comprises any amino acid or may be absent

<400> SEQUENCE: 12

Gly Ile Ile Asn Thr Leu Gln Lys Tyr Tyr Trp Arg Val Arg Gly Gly
1               5                   10                  15

Arg Trp Ala Val Leu Ser Trp Leu Pro Lys Glu Glu Gln Ile Gly Lys
            20                  25                  30

Trp Ser Thr Arg Gly Arg Lys Trp Trp Arg Arg Xaa Xaa
        35                  40                  45

<210> SEQ ID NO 13
<211> LENGTH: 45
<212> TYPE: PRT
<213> ORGANISM: Artificial Sequence
<220> FEATURE:
<223> OTHER INFORMATION: hBD3 derived peptide, C replaced with F
<220> FEATURE:
<221> NAME/KEY: MISC_FEATURE
<222> LOCATION: (44)..(45)
<223> OTHER INFORMATION: Xaa comprises any amino acid or may be absent

<400> SEQUENCE: 13

Gly Ile Ile Asn Thr Leu Gln Lys Tyr Tyr Phe Arg Val Arg Gly Gly
1               5                   10                  15

Arg Phe Ala Val Leu Ser Phe Leu Pro Lys Glu Glu Gln Ile Gly Lys
            20                  25                  30

Phe Ser Thr Arg Gly Arg Lys Phe Phe Arg Arg Xaa Xaa
        35                  40                  45

<210> SEQ ID NO 14
```

-continued

```
<211> LENGTH: 45
<212> TYPE: PRT
<213> ORGANISM: Artificial Sequence
<220> FEATURE:
<223> OTHER INFORMATION: hBD3 derived peptide, C replaced with Y
<220> FEATURE:
<221> NAME/KEY: MISC_FEATURE
<222> LOCATION: (44)..(45)
<223> OTHER INFORMATION: Xaa comprises any amino acid or may be absent

<400> SEQUENCE: 14

Gly Ile Ile Asn Thr Leu Gln Lys Tyr Tyr Tyr Arg Val Arg Gly Gly
1               5                   10                  15

Arg Tyr Ala Val Leu Ser Tyr Leu Pro Lys Glu Glu Gln Ile Gly Lys
            20                  25                  30

Tyr Ser Thr Arg Gly Arg Lys Tyr Tyr Arg Arg Xaa Xaa
        35                  40                  45

<210> SEQ ID NO 15
<211> LENGTH: 45
<212> TYPE: PRT
<213> ORGANISM: Artificial Sequence
<220> FEATURE:
<223> OTHER INFORMATION: hBD3 derived peptide, C replaced with S
<220> FEATURE:
<221> NAME/KEY: MISC_FEATURE
<222> LOCATION: (44)..(45)
<223> OTHER INFORMATION: Xaa comprises any amino acid or may be absent

<400> SEQUENCE: 15

Gly Ile Ile Asn Thr Leu Gln Lys Tyr Tyr Ser Arg Val Arg Gly Gly
1               5                   10                  15

Arg Ser Ala Val Leu Ser Ser Leu Pro Lys Glu Glu Gln Ile Gly Lys
            20                  25                  30

Ser Ser Thr Arg Gly Arg Lys Ser Ser Arg Arg Xaa Xaa
        35                  40                  45

<210> SEQ ID NO 16
<211> LENGTH: 45
<212> TYPE: PRT
<213> ORGANISM: Artificial Sequence
<220> FEATURE:
<223> OTHER INFORMATION: hBD3 derived peptide, C replaced with A
<220> FEATURE:
<221> NAME/KEY: MISC_FEATURE
<222> LOCATION: (44)..(45)
<223> OTHER INFORMATION: Xaa comprises any amino acid or may be absent

<400> SEQUENCE: 16

Gly Ile Ile Asn Thr Leu Gln Lys Tyr Tyr Ala Arg Val Arg Gly Gly
1               5                   10                  15

Arg Ala Ala Val Leu Ser Ala Leu Pro Lys Glu Glu Gln Ile Gly Lys
            20                  25                  30

Ala Ser Thr Arg Gly Arg Lys Ala Ala Arg Arg Xaa Xaa
        35                  40                  45

<210> SEQ ID NO 17
<211> LENGTH: 45
<212> TYPE: PRT
<213> ORGANISM: Artificial Sequence
<220> FEATURE:
<223> OTHER INFORMATION: hBD3 derived peptide, C replaced with C(Acm)
<220> FEATURE:
<221> NAME/KEY: MISC_FEATURE
<222> LOCATION: (11)..(41)
<223> OTHER INFORMATION: Xaa comprises C(Acm)
<220> FEATURE:
```

```
<221> NAME/KEY: MISC_FEATURE
<222> LOCATION: (44)..(45)
<223> OTHER INFORMATION: Xaa comprises any amino acid or may be absent

<400> SEQUENCE: 17

Gly Ile Ile Asn Thr Leu Gln Lys Tyr Tyr Xaa Arg Val Arg Gly Gly
1               5                   10                  15

Arg Xaa Xaa Val Leu Ser Ala Leu Pro Lys Glu Glu Gln Ile Gly Lys
            20                  25                  30

Xaa Ser Thr Arg Gly Arg Lys Xaa Xaa Arg Arg Xaa Xaa
        35                  40                  45

<210> SEQ ID NO 18
<211> LENGTH: 45
<212> TYPE: PRT
<213> ORGANISM: Artificial Sequence
<220> FEATURE:
<223> OTHER INFORMATION: hBD3 derived peptide, C replaced with C(But)
      and terminal KK replaced with XX
<220> FEATURE:
<221> NAME/KEY: MISC_FEATURE
<222> LOCATION: (11)..(41)
<223> OTHER INFORMATION: Xaa comprises C(But)
<220> FEATURE:
<221> NAME/KEY: MISC_FEATURE
<222> LOCATION: (44)..(45)
<223> OTHER INFORMATION: Xaa comprises any amino acid or may be absent

<400> SEQUENCE: 18

Gly Ile Ile Asn Thr Leu Gln Lys Tyr Tyr Xaa Arg Val Arg Gly Gly
1               5                   10                  15

Arg Xaa Xaa Val Leu Ser Ala Leu Pro Lys Glu Glu Gln Ile Gly Lys
            20                  25                  30

Xaa Ser Thr Arg Gly Arg Lys Xaa Xaa Arg Arg Xaa Xaa
        35                  40                  45

<210> SEQ ID NO 19
<211> LENGTH: 45
<212> TYPE: PRT
<213> ORGANISM: Artificial Sequence
<220> FEATURE:
<223> OTHER INFORMATION: hBD3 derived peptide, C replaced with
      C(t-Buthio)
<220> FEATURE:
<221> NAME/KEY: MISC_FEATURE
<222> LOCATION: (11)..(41)
<223> OTHER INFORMATION: Xaa comprises C(t-Buthio)
<220> FEATURE:
<221> NAME/KEY: MISC_FEATURE
<222> LOCATION: (44)..(45)
<223> OTHER INFORMATION: Xaa comprises any amino acid or may be absent

<400> SEQUENCE: 19

Gly Ile Ile Asn Thr Leu Gln Lys Tyr Tyr Xaa Arg Val Arg Gly Gly
1               5                   10                  15

Arg Xaa Xaa Val Leu Ser Ala Leu Pro Lys Glu Glu Gln Ile Gly Lys
            20                  25                  30

Xaa Ser Thr Arg Gly Arg Lys Xaa Xaa Arg Arg Xaa Xaa
        35                  40                  45

<210> SEQ ID NO 20
<211> LENGTH: 45
<212> TYPE: PRT
<213> ORGANISM: Artificial Sequence
<220> FEATURE:
<223> OTHER INFORMATION: hBD3 derived peptide, C replaced with C(Bzl)
      and terminal KK replaced with XX
```

```
<220> FEATURE:
<221> NAME/KEY: MISC_FEATURE
<222> LOCATION: (11)..(41)
<223> OTHER INFORMATION: Xaa comprises C(Bzl)
<220> FEATURE:
<221> NAME/KEY: MISC_FEATURE
<222> LOCATION: (44)..(45)
<223> OTHER INFORMATION: Xaa comprises any amino acid or may be absent

<400> SEQUENCE: 20

Gly Ile Ile Asn Thr Leu Gln Lys Tyr Tyr Xaa Arg Val Arg Gly Gly
1               5                   10                  15

Arg Xaa Xaa Val Leu Ser Ala Leu Pro Lys Glu Glu Gln Ile Gly Lys
            20                  25                  30

Xaa Ser Thr Arg Gly Arg Lys Xaa Xaa Arg Arg Xaa Xaa
        35                  40                  45

<210> SEQ ID NO 21
<211> LENGTH: 45
<212> TYPE: PRT
<213> ORGANISM: Artificial Sequence
<220> FEATURE:
<223> OTHER INFORMATION: hBD3 derived peptide, C replaced with
      C(4-MeBzl) and terminal KK replaced with XX
<220> FEATURE:
<221> NAME/KEY: MISC_FEATURE
<222> LOCATION: (11)..(41)
<223> OTHER INFORMATION: Xaa comprises C(4-MeBzl)
<220> FEATURE:
<221> NAME/KEY: MISC_FEATURE
<222> LOCATION: (44)..(45)
<223> OTHER INFORMATION: Xaa comprises any amino acid or may be absent

<400> SEQUENCE: 21

Gly Ile Ile Asn Thr Leu Gln Lys Tyr Tyr Xaa Arg Val Arg Gly Gly
1               5                   10                  15

Arg Xaa Xaa Val Leu Ser Ala Leu Pro Lys Glu Glu Gln Ile Gly Lys
            20                  25                  30

Xaa Ser Thr Arg Gly Arg Lys Xaa Xaa Arg Arg Xaa Xaa
        35                  40                  45

<210> SEQ ID NO 22
<211> LENGTH: 45
<212> TYPE: PRT
<213> ORGANISM: Artificial Sequence
<220> FEATURE:
<223> OTHER INFORMATION: hBD3 derived peptide, C replaced with
      C(4-MeO-Bzl) and terminal KK replaced with XX
<220> FEATURE:
<221> NAME/KEY: MISC_FEATURE
<222> LOCATION: (11)..(41)
<223> OTHER INFORMATION: Xaa comprises C(4-MeO-Bzl)
<220> FEATURE:
<221> NAME/KEY: MISC_FEATURE
<222> LOCATION: (44)..(45)
<223> OTHER INFORMATION: Xaa comprises any amino acid or may be absent

<400> SEQUENCE: 22

Gly Ile Ile Asn Thr Leu Gln Lys Tyr Tyr Xaa Arg Val Arg Gly Gly
1               5                   10                  15

Arg Xaa Xaa Val Leu Ser Ala Leu Pro Lys Glu Glu Gln Ile Gly Lys
            20                  25                  30

Xaa Ser Thr Arg Gly Arg Lys Xaa Xaa Arg Arg Xaa Xaa
        35                  40                  45

<210> SEQ ID NO 23
<211> LENGTH: 45
```

```
<212> TYPE: PRT
<213> ORGANISM: Artificial Sequence
<220> FEATURE:
<223> OTHER INFORMATION: hBD3 derived peptide, C replaced with C(Mmt)
      and terminal KK replaced with XX
<220> FEATURE:
<221> NAME/KEY: MISC_FEATURE
<222> LOCATION: (11)..(41)
<223> OTHER INFORMATION: Xaa comprises C(Mmt)
<220> FEATURE:
<221> NAME/KEY: MISC_FEATURE
<222> LOCATION: (44)..(45)
<223> OTHER INFORMATION: Xaa comprises any amino acid or may be absent

<400> SEQUENCE: 23

Gly Ile Ile Asn Thr Leu Gln Lys Tyr Tyr Xaa Arg Val Arg Gly Gly
1               5                   10                  15

Arg Xaa Xaa Val Leu Ser Ala Leu Pro Lys Glu Glu Gln Ile Gly Lys
            20                  25                  30

Xaa Ser Thr Arg Gly Arg Lys Xaa Xaa Arg Arg Xaa Xaa
        35                  40                  45

<210> SEQ ID NO 24
<211> LENGTH: 45
<212> TYPE: PRT
<213> ORGANISM: Artificial Sequence
<220> FEATURE:
<223> OTHER INFORMATION: hBD3 derived peptide, C replaced with any
      modified C
<220> FEATURE:
<221> NAME/KEY: MISC_FEATURE
<222> LOCATION: (11)..(41)
<223> OTHER INFORMATION: Xaa comprises C(Cam), C(But), C(t-Buthio),
      C(Bzl), C(4-MeBzl), C(4-MeOBzl) or C(Mmt)
<220> FEATURE:
<221> NAME/KEY: MISC_FEATURE
<222> LOCATION: (44)..(45)
<223> OTHER INFORMATION: Xaa comprises any amino acid or may be absent

<400> SEQUENCE: 24

Gly Ile Ile Asn Thr Leu Gln Lys Tyr Tyr Xaa Arg Val Arg Gly Gly
1               5                   10                  15

Arg Xaa Xaa Val Leu Ser Ala Leu Pro Lys Glu Glu Gln Ile Gly Lys
            20                  25                  30

Xaa Ser Thr Arg Gly Arg Lys Xaa Xaa Arg Arg Xaa Xaa
        35                  40                  45

<210> SEQ ID NO 25
<211> LENGTH: 10
<212> TYPE: PRT
<213> ORGANISM: Artificial Sequence
<220> FEATURE:
<223> OTHER INFORMATION: hBD3 derived C terminus 10 aa fragment C
      replaced with X
<220> FEATURE:
<221> NAME/KEY: MISC_FEATURE
<222> LOCATION: (5)..(6)
<223> OTHER INFORMATION: Xaa comprises any amino acid
<220> FEATURE:
<221> NAME/KEY: MISC_FEATURE
<222> LOCATION: (9)..(10)
<223> OTHER INFORMATION: Xaa comprises any amino acid or may be absent

<400> SEQUENCE: 25

Arg Gly Arg Lys Xaa Xaa Arg Arg Xaa Xaa
1               5                   10

<210> SEQ ID NO 26
<211> LENGTH: 10
```

```
<212> TYPE: PRT
<213> ORGANISM: Artificial Sequence
<220> FEATURE:
<223> OTHER INFORMATION: hBD3 derived C terminus 10 aa fragment C
      replaced with W
<220> FEATURE:
<221> NAME/KEY: MISC_FEATURE
<222> LOCATION: (9)..(10)
<223> OTHER INFORMATION: Xaa comprises any amino acid or may be absent

<400> SEQUENCE: 26

Arg Gly Arg Lys Trp Trp Arg Arg Xaa Xaa
1               5                   10

<210> SEQ ID NO 27
<211> LENGTH: 10
<212> TYPE: PRT
<213> ORGANISM: Artificial Sequence
<220> FEATURE:
<223> OTHER INFORMATION: hBD3 derived C terminus 10 aa fragment C
      replaced with F
<220> FEATURE:
<221> NAME/KEY: MISC_FEATURE
<222> LOCATION: (9)..(10)
<223> OTHER INFORMATION: Xaa comprises any amino acid or may be absent

<400> SEQUENCE: 27

Arg Gly Arg Lys Phe Phe Arg Arg Xaa Xaa
1               5                   10

<210> SEQ ID NO 28
<211> LENGTH: 10
<212> TYPE: PRT
<213> ORGANISM: Artificial Sequence
<220> FEATURE:
<223> OTHER INFORMATION: hBD3 derived C terminus 10 aa fragment C
      replaced with Y
<220> FEATURE:
<221> NAME/KEY: MISC_FEATURE
<222> LOCATION: (9)..(10)
<223> OTHER INFORMATION: Xaa comprises any amino acid or may be absent

<400> SEQUENCE: 28

Arg Gly Arg Lys Tyr Tyr Arg Arg Xaa Xaa
1               5                   10

<210> SEQ ID NO 29
<211> LENGTH: 10
<212> TYPE: PRT
<213> ORGANISM: Artificial Sequence
<220> FEATURE:
<223> OTHER INFORMATION: hBD3 derived C terminus 10 aa fragment C
      replaced with L
<220> FEATURE:
<221> NAME/KEY: MISC_FEATURE
<222> LOCATION: (9)..(10)
<223> OTHER INFORMATION: Xaa may comprise any amino acid or may be
      absent

<400> SEQUENCE: 29

Arg Gly Arg Lys Leu Leu Arg Arg Xaa Xaa
1               5                   10

<210> SEQ ID NO 30
<211> LENGTH: 10
<212> TYPE: PRT
<213> ORGANISM: Artificial Sequence
<220> FEATURE:
<223> OTHER INFORMATION: hBD3 derived C terminus 10 aa fragment C
      replaced with I
<220> FEATURE:
```

```
<221> NAME/KEY: MISC_FEATURE
<222> LOCATION: (9)..(10)
<223> OTHER INFORMATION: Xaa comprises any amino acid or may be absent

<400> SEQUENCE: 30

Arg Gly Arg Lys Ile Ile Arg Arg Xaa Xaa
1               5                   10

<210> SEQ ID NO 31
<211> LENGTH: 10
<212> TYPE: PRT
<213> ORGANISM: Artificial Sequence
<220> FEATURE:
<223> OTHER INFORMATION: hBD3 derived C terminus 10 aa fragment C
      replaced with H
<220> FEATURE:
<221> NAME/KEY: MISC_FEATURE
<222> LOCATION: (9)..(10)
<223> OTHER INFORMATION: Xaa comprises any amino acid or may be absent

<400> SEQUENCE: 31

Arg Gly Arg Lys His His Arg Arg Xaa Xaa
1               5                   10

<210> SEQ ID NO 32
<211> LENGTH: 10
<212> TYPE: PRT
<213> ORGANISM: Artificial Sequence
<220> FEATURE:
<223> OTHER INFORMATION: hBD3 derived C terminus 10 aa fragment C
      modified
<220> FEATURE:
<221> NAME/KEY: MISC_FEATURE
<222> LOCATION: (5)..(6)
<223> OTHER INFORMATION: Xaa comprises C(But), C(t-Buthio), C(Bzl),
      C(4-MeBzl), C(4-MeOBzl) or C(Mmt)
<220> FEATURE:
<221> NAME/KEY: MISC_FEATURE
<222> LOCATION: (9)..(10)
<223> OTHER INFORMATION: Xaa comprises any amino acid or may be absent

<400> SEQUENCE: 32

Arg Gly Arg Lys Xaa Xaa Arg Arg Xaa Xaa
1               5                   10

<210> SEQ ID NO 33
<211> LENGTH: 10
<212> TYPE: PRT
<213> ORGANISM: Artificial Sequence
<220> FEATURE:
<223> OTHER INFORMATION: hBD3 derived C terminus 10 aa fragment C
      replaced with V
<220> FEATURE:
<221> NAME/KEY: MISC_FEATURE
<222> LOCATION: (9)..(10)
<223> OTHER INFORMATION: Xaa comprises any amino acid or may be absent

<400> SEQUENCE: 33

Arg Gly Arg Lys Val Val Arg Arg Xaa Xaa
1               5                   10

<210> SEQ ID NO 34
<211> LENGTH: 10
<212> TYPE: PRT
<213> ORGANISM: Artificial Sequence
<220> FEATURE:
<223> OTHER INFORMATION: hBD3 derived C terminus 10 aa fragment
<220> FEATURE:
<221> NAME/KEY: MISC_FEATURE
<222> LOCATION: (9)..(10)
<223> OTHER INFORMATION: Xaa comprises any amino acid or may be absent
```

<400> SEQUENCE: 34

Arg Gly Arg Lys Cys Cys Arg Arg Xaa Xaa
1               5                   10

<210> SEQ ID NO 35
<211> LENGTH: 10
<212> TYPE: PRT
<213> ORGANISM: Artificial Sequence
<220> FEATURE:
<223> OTHER INFORMATION: hBD3 derived C terminus, C modified
<220> FEATURE:
<221> NAME/KEY: MISC_FEATURE
<222> LOCATION: (5)..(6)
<223> OTHER INFORMATION: Xaa comprises C(Acm), C(But), C(t-Buthio),
      C(Bzl), C(4-MeBzl), C(4-MeOBzl) or C(Mmt)
<220> FEATURE:
<221> NAME/KEY: MISC_FEATURE
<222> LOCATION: (9)..(10)
<223> OTHER INFORMATION: Xaa may comprise any amino acid or may be
      absent.

<400> SEQUENCE: 35

Arg Gly Arg Lys Xaa Xaa Arg Arg Lys Lys
1               5                   10

<210> SEQ ID NO 36
<211> LENGTH: 8
<212> TYPE: PRT
<213> ORGANISM: Artificial Sequence
<220> FEATURE:
<223> OTHER INFORMATION: hBD3 repeated fragment excluding terminal KK,
      C residues replaced with X
<220> FEATURE:
<221> NAME/KEY: MISC_FEATURE
<222> LOCATION: (5)..(6)
<223> OTHER INFORMATION: Xaa comprises any amino acid

<400> SEQUENCE: 36

Arg Gly Arg Lys Xaa Xaa Arg Arg
1               5

<210> SEQ ID NO 37
<211> LENGTH: 8
<212> TYPE: PRT
<213> ORGANISM: Artificial Sequence
<220> FEATURE:
<223> OTHER INFORMATION: hBD3 repeated fragment excluding terminal KK,
      C residues replaced with W

<400> SEQUENCE: 37

Arg Gly Arg Lys Trp Trp Arg Arg
1               5

<210> SEQ ID NO 38
<211> LENGTH: 8
<212> TYPE: PRT
<213> ORGANISM: Artificial Sequence
<220> FEATURE:
<223> OTHER INFORMATION: hBD3 repeated fragment excluding terminal KK,
      C residues replaced with F

<400> SEQUENCE: 38

Arg Gly Arg Lys Phe Phe Arg Arg
1               5

<210> SEQ ID NO 39
<211> LENGTH: 8
<212> TYPE: PRT

```
<213> ORGANISM: Artificial Sequence
<220> FEATURE:
<223> OTHER INFORMATION: hBD3 repeated fragment excluding terminal KK,
      C residues replaced with Y

<400> SEQUENCE: 39

Arg Gly Arg Lys Tyr Tyr Arg Arg
1               5

<210> SEQ ID NO 40
<211> LENGTH: 8
<212> TYPE: PRT
<213> ORGANISM: Artificial Sequence
<220> FEATURE:
<223> OTHER INFORMATION: hBD3 repeated fragment excluding terminal KK,
      C residues replaced with L

<400> SEQUENCE: 40

Arg Gly Arg Lys Leu Leu Arg Arg
1               5

<210> SEQ ID NO 41
<211> LENGTH: 8
<212> TYPE: PRT
<213> ORGANISM: Artificial Sequence
<220> FEATURE:
<223> OTHER INFORMATION: hBD3 repeated fragment excluding terminal KK,
      C residues replaced with I

<400> SEQUENCE: 41

Arg Gly Arg Lys Ile Ile Arg Arg
1               5

<210> SEQ ID NO 42
<211> LENGTH: 8
<212> TYPE: PRT
<213> ORGANISM: Artificial Sequence
<220> FEATURE:
<223> OTHER INFORMATION: hBD3 repeated fragment excluding terminal KK,
      C residues replaced with H

<400> SEQUENCE: 42

Arg Gly Arg Lys His His Arg Arg
1               5

<210> SEQ ID NO 43
<211> LENGTH: 8
<212> TYPE: PRT
<213> ORGANISM: Artificial Sequence
<220> FEATURE:
<223> OTHER INFORMATION: hBD3 repeated fragment excluding terminal KK,
      C residues replaced with C(Acm)
<220> FEATURE:
<221> NAME/KEY: MISC_FEATURE
<222> LOCATION: (5)..(6)
<223> OTHER INFORMATION: Xaa comprises C(Acm), C(But), C(t-Buthio),
      C(Bzl), C(4-MeBzl), C(4-MeOBzl) or C(Mmt).

<400> SEQUENCE: 43

Arg Gly Arg Lys Xaa Xaa Arg Arg
1               5

<210> SEQ ID NO 44
<211> LENGTH: 8
<212> TYPE: PRT
<213> ORGANISM: Artificial Sequence
<220> FEATURE:
<223> OTHER INFORMATION: hBD3 repeated fragment excluding terminal KK,
      C residues replaced with V
```

```
<400> SEQUENCE: 44

Arg Gly Arg Lys Val Val Arg Arg
1               5

<210> SEQ ID NO 45
<211> LENGTH: 10
<212> TYPE: PRT
<213> ORGANISM: Artificial Sequence
<220> FEATURE:
<223> OTHER INFORMATION: hBD3 derived peptide, V2 monomer and KK
      residues. 10 aa

<400> SEQUENCE: 45

Arg Gly Arg Lys Val Val Arg Arg Lys Lys
1               5                   10

<210> SEQ ID NO 46
<211> LENGTH: 10
<212> TYPE: PRT
<213> ORGANISM: Artificial Sequence
<220> FEATURE:
<223> OTHER INFORMATION: V4 monomer, V4-10 AA

<400> SEQUENCE: 46

Arg Gly Arg Lys Val Val Arg Arg Val Val
1               5                   10

<210> SEQ ID NO 47
<211> LENGTH: 10
<212> TYPE: PRT
<213> ORGANISM: Artificial Sequence
<220> FEATURE:
<223> OTHER INFORMATION: Y4 monomer (Y4-10 AA)

<400> SEQUENCE: 47

Arg Gly Arg Lys Tyr Tyr Arg Arg Tyr Tyr
1               5                   10

<210> SEQ ID NO 48
<211> LENGTH: 10
<212> TYPE: PRT
<213> ORGANISM: Artificial Sequence
<220> FEATURE:
<223> OTHER INFORMATION: W4 monomer, W4-10 AA

<400> SEQUENCE: 48

Arg Gly Arg Lys Trp Trp Arg Arg Trp Trp
1               5                   10

<210> SEQ ID NO 49
<211> LENGTH: 8
<212> TYPE: PRT
<213> ORGANISM: Artificial Sequence
<220> FEATURE:
<223> OTHER INFORMATION: hBD3 derived peptide, V3 monomer

<400> SEQUENCE: 49

Arg Val Arg Lys Val Val Arg Arg
1               5

<210> SEQ ID NO 50
<211> LENGTH: 8
<212> TYPE: PRT
<213> ORGANISM: Artificial Sequence
<220> FEATURE:
<223> OTHER INFORMATION: hBD3 derived peptide, V2R monomer
```

```
<400> SEQUENCE: 50

Arg Arg Arg Lys Val Val Arg Arg
1               5

<210> SEQ ID NO 51
<211> LENGTH: 8
<212> TYPE: PRT
<213> ORGANISM: Artificial Sequence
<220> FEATURE:
<223> OTHER INFORMATION: hBD3 derived peptide, V2D monomer

<400> SEQUENCE: 51

Arg Asp Arg Lys Val Val Arg Arg
1               5

<210> SEQ ID NO 52
<211> LENGTH: 8
<212> TYPE: PRT
<213> ORGANISM: Artificial Sequence
<220> FEATURE:
<223> OTHER INFORMATION: hBD3 derived peptide, E2 monomer

<400> SEQUENCE: 52

Arg Gly Arg Lys Glu Glu Arg Arg
1               5

<210> SEQ ID NO 53
<211> LENGTH: 8
<212> TYPE: PRT
<213> ORGANISM: Artificial Sequence
<220> FEATURE:
<223> OTHER INFORMATION: hBD3 derived peptide, K2 monomer

<400> SEQUENCE: 53

Arg Gly Arg Lys Lys Lys Arg Arg
1               5

<210> SEQ ID NO 54
<211> LENGTH: 10
<212> TYPE: PRT
<213> ORGANISM: Artificial Sequence
<220> FEATURE:
<223> OTHER INFORMATION: peptide comprising 10 arginines (R)

<400> SEQUENCE: 54

Arg Arg Arg Arg Arg Arg Arg Arg Arg Arg
1               5                   10

<210> SEQ ID NO 55
<211> LENGTH: 4
<212> TYPE: PRT
<213> ORGANISM: Artificial Sequence
<220> FEATURE:
<223> OTHER INFORMATION: peptide comprising 4 valines (V)

<400> SEQUENCE: 55

Val Val Val Val
1

<210> SEQ ID NO 56
<211> LENGTH: 4
<212> TYPE: PRT
<213> ORGANISM: Artificial Sequence
<220> FEATURE:
<223> OTHER INFORMATION: peptide comprising 4 tyrosines (Y)
```

```
<400> SEQUENCE: 56

Tyr Tyr Tyr Tyr
1

<210> SEQ ID NO 57
<211> LENGTH: 8
<212> TYPE: PRT
<213> ORGANISM: Artificial Sequence
<220> FEATURE:
<223> OTHER INFORMATION: SEQ ID NO: 44 in reverse

<400> SEQUENCE: 57

Arg Arg Val Val Lys Arg Gly Arg
1               5

<210> SEQ ID NO 58
<211> LENGTH: 9
<212> TYPE: PRT
<213> ORGANISM: Artificial Sequence
<220> FEATURE:
<223> OTHER INFORMATION: SEQ ID NO: 57 + K

<400> SEQUENCE: 58

Arg Arg Val Val Lys Arg Gly Arg Lys
1               5
```

MULTIMERIC FORMS OF ANTIMICROBIAL PEPTIDES

CROSS REFERENCE TO RELATED APPLICATIONS

This application is a National Stage Entry of PCT/SG2009/000144, filed Apr. 21, 2009, which claims priority to U.S. Provisional Application No. 61/046,584, filed Apr. 21, 2008, which are each incorporated by reference for all purposes.

FIELD OF THE INVENTION

The present invention relates to novel multimeric forms of peptides with antimicrobial properties. The invention also relates to methods of making these multimers. The invention relates to the use of these multimers for inhibiting the growth of a broad spectrum of microorganisms. The invention further relates to compositions comprising these peptides.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: LWIS_003_01US_SeqList.txt, date recorded: Oct. 21, 2010, file size 25 kilobytes).

BACKGROUND OF THE INVENTION

Defensins are cationic antimicrobial peptides and are components of the innate immune system. In humans, the alpha defensins are produced by neutrophils or the Paneth cells of the intestinal tract while the beta defensins are produced by epithelial cells. Defensins have broad spectrum anti-microbial properties against gram negative and gram positive bacteria, some fungi as well as enveloped viruses.

The exact mechanism for the anti-microbial properties is not completely understood but the hydrophobicity and the net positive charge of the peptides appear to be important in its interaction and disruption of the microbial cell wall and cell membrane.

Several studies suggest that full length defensins may form dimers at a bacterial membrane but non-covalent forms (Hoover et al., 2000; Hoover et al., 2001 Schibili at al., 2002) and one study suggests that dimerisation may affect antimicrobial properties (Campopiano et al., 2004). However, the properties of these dimers were not studied or characterised in detail.

The development of antibiotic resistance is a challenge in the development of antibiotics. Although the antimicrobial activity of defensins is not completely understood, the possible mode of action of defensins suggests that microbial resistance may develop very slowly or minimally and the potential of using defensins as antimicrobials is promising. However, defensins are also known to have toxicity to host cells, including mammalian cells which may limit their application as antimicrobials.

It is therefore desirable to develop new peptide derivatives of defensins with high antimicrobial activity and low host cell toxicity.

SUMMARY OF THE INVENTION

The present invention relates to isolated multimers derived from hBD3 (SEQ ID NO: 1).

hBD3
(SEQ ID NO: 1)
GIINTLQKYYCRVRGGRCAVLSCLPKEEQIGKCSTRGRKCCRRKK

According to a first aspect, the present invention relates to an isolated multimer of defensin peptides of formula $(U)_n$, wherein U is a peptide comprising SEQ ID NO: 2 or a fragment or variant thereof and $n \geq 2$.

SEQ ID NO: 2
GIINTLQKYYXRVRGGRXAVLSXLPKEEQIGKXSTRGRKXXRRZZ

X comprises any amino acid; Z comprises any amino acid or may be absent. For example, Z may include but is not limited to lysine, ornithine or arginine. In particular, Z may be lysine.

According to another aspect, the present invention relates to an isolated multimer comprising at least two units of a peptide U, wherein the peptide U comprises SEQ ID NO: 2 or a fragment or variant thereof.

The peptide U is repeated in the multimer. In particular, the repeating peptides U are linked together covalently. Further, the peptides U may be linked together through at least one amino acid B. Each B may be an amino acid having at least two amine groups. For example, each B may include but is not limited to lysine, ornithine or arginine.

The repeating unit or the peptide U in any multimer according to the present invention may be any peptide described in WO 2007/126392.

The peptide U may include peptide fragments derived from SEQ ID NO: 2. The fragments may be fragments of any length derived from SEQ ID NO: 2. In particular, the peptide U may comprise SEQ ID NO: 3 or a fragment or variant thereof.

SEQ ID NO: 3
GIINTLQKYYXRVRGGRXAVLSXLPKEEQIGKXSTRGRKXXRR
X comprises any amino acid.

The peptide U of the multimer may have a charge of +1 to +11.

According to another aspect, the invention relates to an isolated multimer of formula $(U)_n B_m Z_j$, wherein U comprises SEQ ID NO: 3 or a fragment or variant thereof, each B comprises at least one amino acid residue comprising at least two amine groups, Z comprises any amino acid, $n \geq 2$, $m \geq 1$ and $j \geq 0$. B may comprise an amino acid having at least two amine groups. sln particular, each B includes but is not limited to lysine, ornithine or arginine.

According to one aspect of the invention, the B and Z in $(U)_n B_m Z_j$ may both comprise lysine (K) and the formula may be expressed as $(U)_n K_m K_j$. According to a further aspect, m may also equal the number n−1 and j may equal to 1 and the formula of the multimer may be expressed as $(U)_n K_{n-1} K$ (or $(UK)_n$. The peptide U in $(U)_n K_m K_j$ or $(U)_n K_{n-1} K$ may comprise SEQ ID NO: 3 or a fragment or variant thereof.

The multimer(s) of the invention may be linear or branched. If the multimer $(U)_n$ is linear, the peptide U repeated n times may comprise SEQ ID NO: 2 or any fragment or variant of SEQ ID NO: 2.

For a branched multimer, for example the multimer $(U)_nB_mZ_j$, the multimer may be branched at the terminal $B_mZ_j$ residues.

The multimers according to the invention may comprise any number of repeating units of the peptide U. For example, the multimer may comprise 2 to 10, 2 to 20, 2 to 30 repeating units of the peptide U. Further, the multimer may be a dimer, trimer, tetramer, pentamer, hexamer, heptamer, octamer, nonamer and decamer. In particular, n may be an even number. More in particular, n may comprise any number starting from 2 and increasing in multiples of 2.

Further, any amino acid residue of the multimer may comprise an amino acid having at least one protecting group. The protecting groups may comprise Boc, But, Fmoc, Pbf or any other protecting group.

The invention also relates to a method of preparing at least one multimer of the invention.

Accordingly, the invention relates to a method of preparing at least one multimer of formula $(U)_n$, wherein U is a peptide comprising SEQ ID NO: 2 or a fragment or variant thereof, the method comprising linking at least two units of U together.

The multimer(s) of the invention may also be produced by recombinant DNA technology. Any part or the whole of the multimer(s) of the invention may be produced by recombinant DNA technology. For example, the peptide monomers may be synthesised separately by recombinant DNA methods and then linked together to form multimers by chemical methods.

Accordingly, the present invention also relates to an isolated nucleic acid molecule encoding any part of or the whole of the multimer(s) of the invention. The nucleic acid molecule(s) may be inserted into a vector. Further, either the nucleic acid molecule(s) or the vector comprising the nucleic acid molecule(s) may be introduced into a host cell for expressing any part of or the whole of the multimer(s) of the invention.

The multimer(s) of the invention may also be produced de novo by chemical synthesis. For example, the multimer(s) of the invention may be produced by a solid phase peptide synthesis (SPPS) method of the invention.

The invention also relates to a method of preparing at least one multimer of formula: $(U)_nB_mZ_j$, wherein U comprises SEQ ID NO: 3 or a fragment or variant thereof, each B comprises an amino acid comprising at least two amine groups, Z comprises any amino acid and $n \geq 2$, $m \geq 1$ and $j \geq 0$.
(i) providing at least one solid phase;
(ii) coupling at least a first amino acid Z to the solid phase;
(iii) linking at least one protected amino acid residue B to the coupled first amino acid residue;
(iv) removing the protecting group(s) from the linked B residue(s)
(v) providing additional chain extension by linking protected amino acid residues, according to the sequence of the peptide U in order from the C-terminus to the N-terminus, wherein after each linking, the protecting groups are removed for the next linking; and
(vi) terminating the linking of amino acid residues depending on the number of residues to be added.

The protected amino acid B comprises at least two side chains protected by protecting groups. In particular, each B includes but is not limited to lysine, ornithine or arginine. The amino acid Z first coupled to the solid phase may also be but is not limited to lysine, ornithine or arginine.

The method may be extended to produce further multimers. For example, the extended method to produce further multimers further comprises, after step (iv)

(iv)(a) linking further protected B residues to the linked B residue(s);
(iv)(b) removing the protecting group(s) from the B residues from (iv)(a);
(iv)(c) repeating step (iv)(a) and (iv)(b), or
(iv)(d) proceeding to step (v) and (vi).

The multimers formed depend on the number of amine groups in B. If the number of amine groups in B is two, for example in lysine (K) or ornithine, the extended method may produce multimers increasing in multiples of two from the previous multimer. The multimers formed from the extended method will be four, eight, sixteen, thirty-two, sixty-four and so on.

If B is arginine (R) which has three amine groups (two primary amine groups and one secondary amine group), the first multimer formed will be a trimer. The subsequent multimers formed using arginine will increase in multiples of three.

For each round of multimerisation, combinations of lysine or ornithine with arginine or vice versa may be used for B, and multimers with different number of repeating units may be produced.

Following completion of the synthesis of the multimer, the multimer may be released from the solid phase.

BRIEF DESCRIPTION OF THE FIGURES

FIG. 1 illustrates the structures of the protected lysine residue Lys(Fmoc), the V2 monomer and the V2 dimer. The lysine (K) residue in bold shows the position which Lys (Fmoc) were incorporated during the synthesis.

Step (i) illustrates the removal of protecting group using 20% piperidine in DMF (N,N-Dimethylformamide).

Step (ii) illustrates the coupling reactions with 0.5 M HBTU (N-[1H-benzotrialzol-1-yl]-(dimethylamino)methylene)-N-methylmethanaminium), 0.5 M HOBT (N-hydrozybenxotrialzole), 2 M DIEA (Diisoproplyethylamine) in NMP (N-methylpyrrolidone).

Fmoc(Lys) is coupled to the lysine residue bound to the resin. Step (i) is repeated. Two arginine residues (R) are then added to each chain.

Step (iii) illustrates chain extension comprising six cycles of SPPS with 0.5 M HBTU/0.5 M HOBT/2 M DIEA to incorporate the remaining amino acids of the V2 dimer.

Step (iv) illustrates the cleavage reaction to release the dimer from the resin using the cleavage agent 90% TFA (trifluoroacetic acid), 5.0% phenol, 1.5% water, 1.0% TIS (triisopropyl silane), 2.5% EDT (ethane dithiol).

RGRKVVRR (SEQ ID NO: 44) is the repeated in the dimer.

Figure 3:
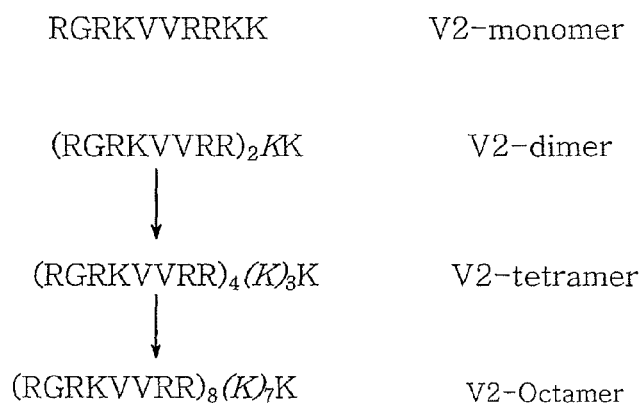

FIG. 3 illustrates that the SPPS method can be used to form multimers increasing in muliples of 2. For example, dimers, tetramers, octamers and further multimers wherein the number of monomer units increases in multples of two may be produced. The lysine (K) residue in bold italics shows the position which Lys(Fmoc) were incorporated during the synthesis.

The sequences in FIG. 3 are:

| RGRKVVRRKK | (SEQ ID NO: 45) |
| RGRKVVRR | (SEQ ID NO: 46) |

Figure 4:
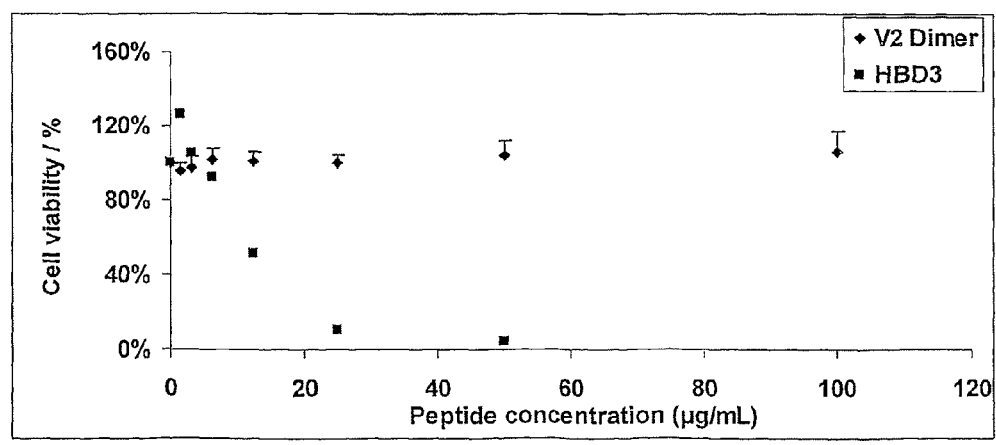

FIG. 4 is a graph which illustrates that the V2 dimer does not show cytotoxicity toward human conjunctival epithelial cells in comparison with native hBD3. The results are from four independent experiments and data points show the mean and standard deviations. The X axis indicates the peptide concentration in µg/ml and the Y axis indicates the % cell viability.

Figure 5:
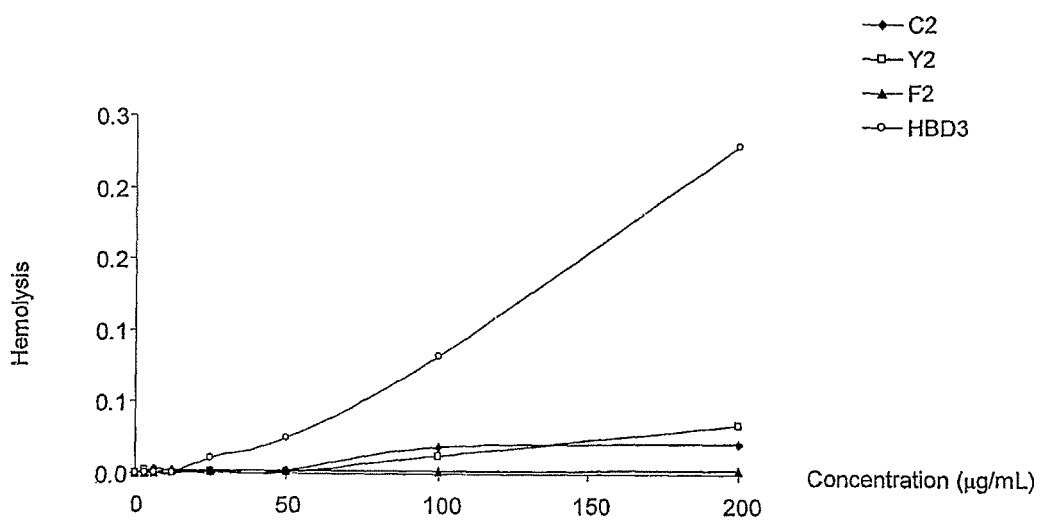

FIG. 5 illustrates the haemolytic effects of wt hBD3 and its C-terminus peptides on rabbit erythrocytes.

Figure 6:
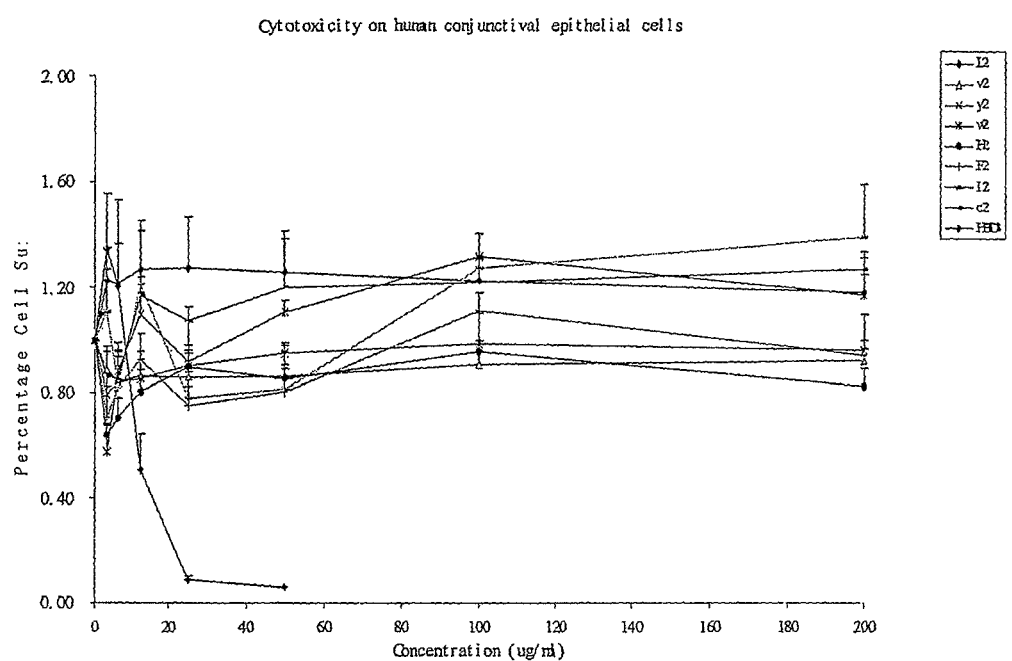

FIG. 6 illustrates the cytotoxicity effects of wt hBFD3 and its C-terminus peptides on human conjunctival epithelial cells.

Figure 7:
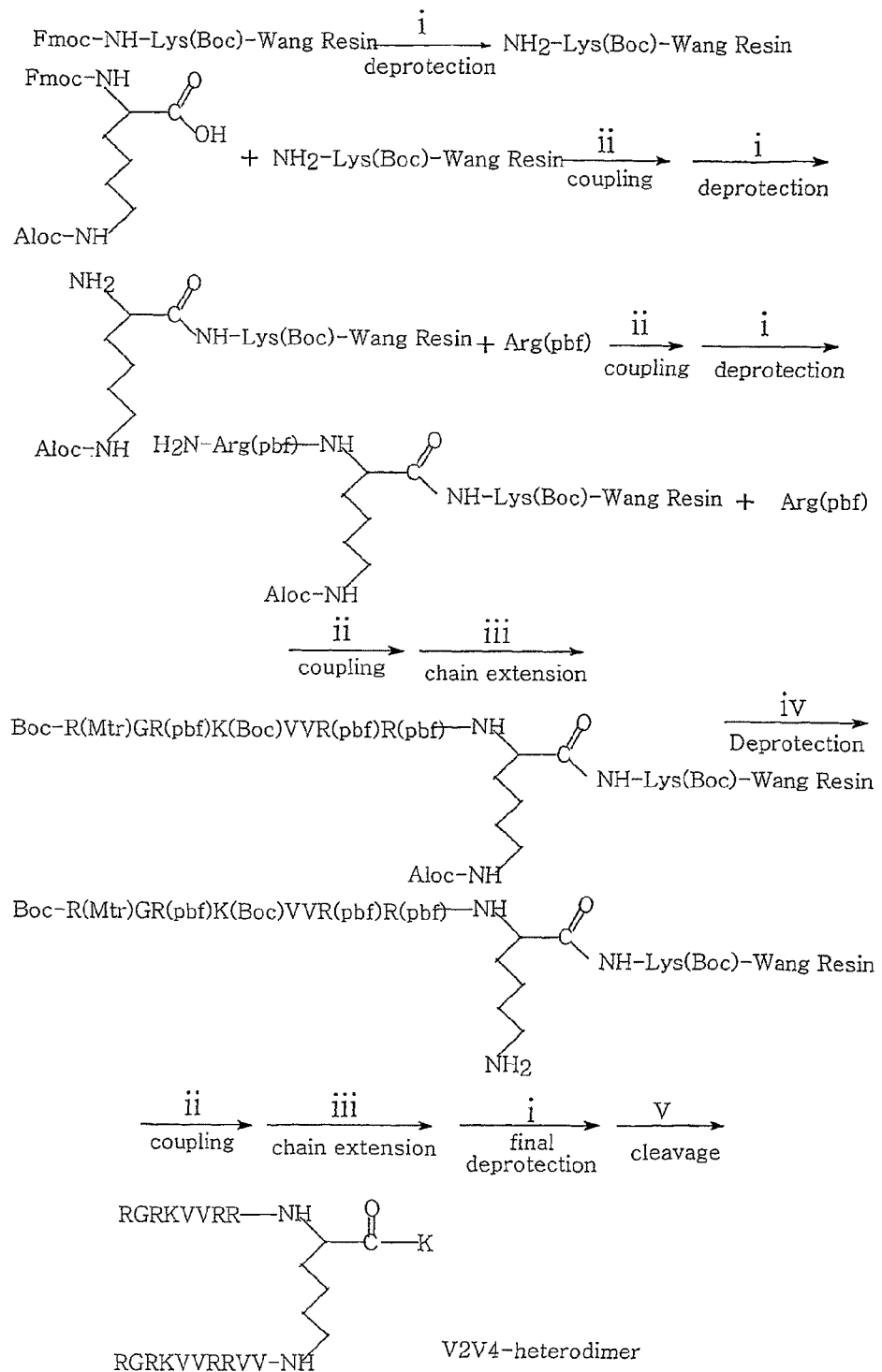

FIG. 7 illustrates an exemplification of a method of preparing a heterodimer.

The sequences in FIG. 7 are:

```
RGRKVVRR        (SEQ ID NO: 44)
RGRKVVRRVV      (SEQ ID NO: 46)
```

Figure 8:
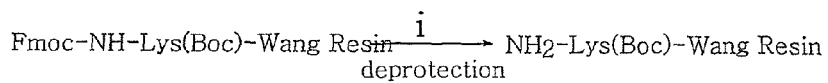
Figure 8:
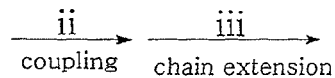
Figure 8:
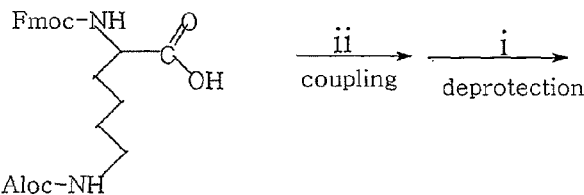
Figure 8:
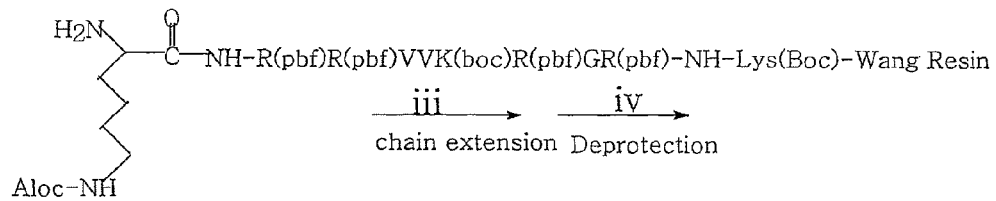
Figure 8:
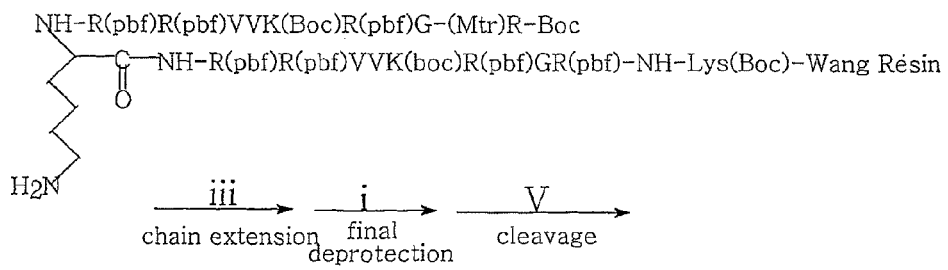
Figure 8:
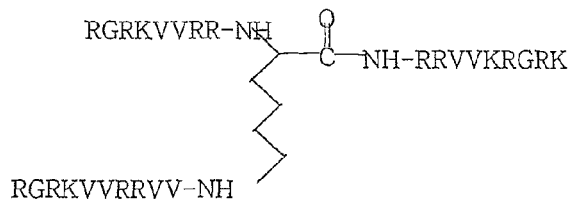

FIG. 8 illustrates an exemplification of a method of preparing a heterotetramer.

The sequences in FIG. 8 are:

```
RRVVKRGRK       (SEQ ID NO: 58)
RGRKVVRR        (SEQ ID NO: 44)
RGRKVVRRVV      (SEQ ID NO: 46)
```

Figure 9:
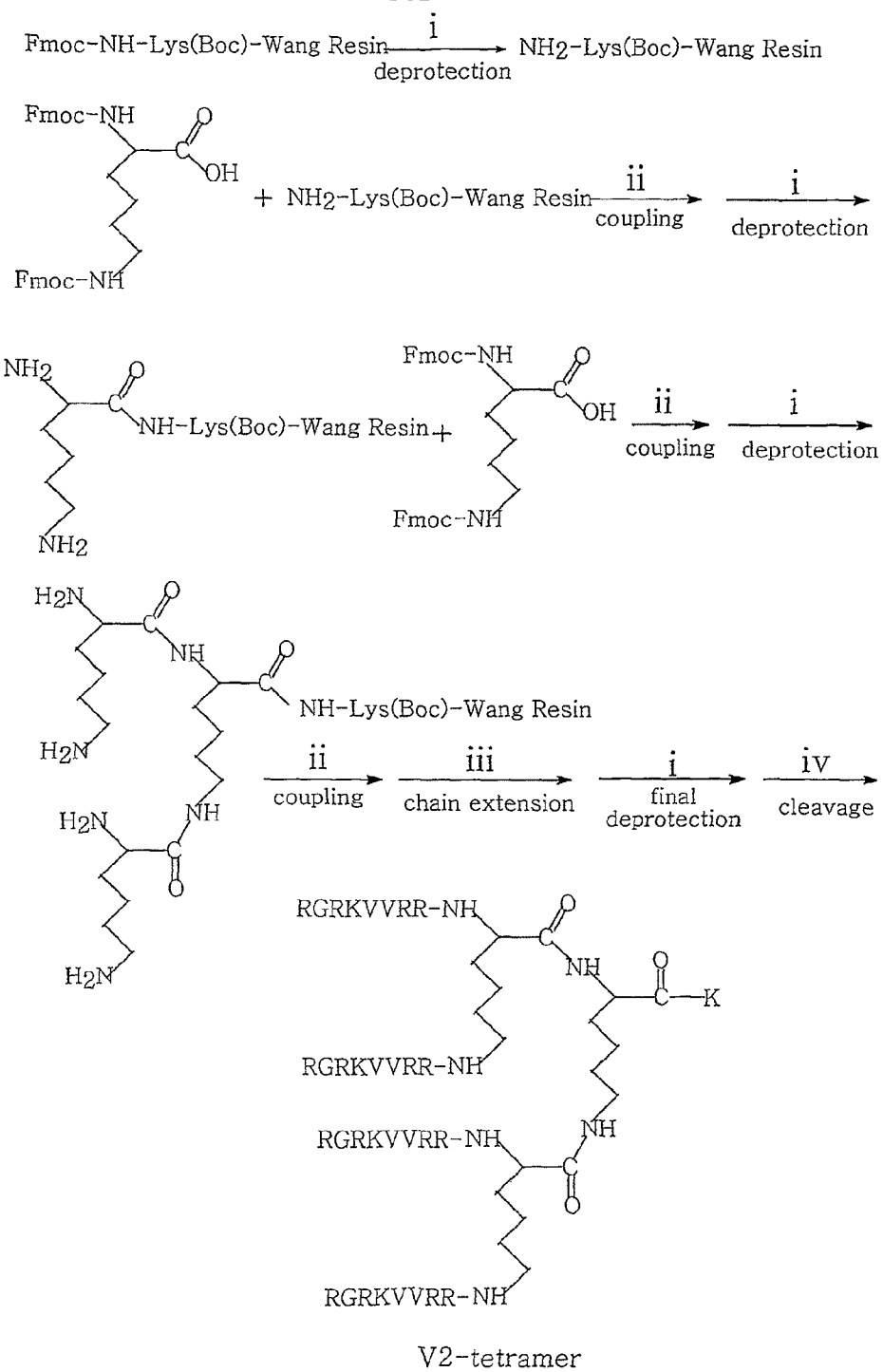

FIG. 9 illustrates an exemplification of a method of preparing a homogeneous tetramer.

DEFINITIONS

Where X is found in a peptide sequence or formula, X represents any amino acid, including protected cysteine residues including but not limited to C(Acm), C(But), C(Cam), C(t-Buthio), C(Bzl), C(4-MeO-Bzl) and C(Mmt).

Variant of a peptide or multimer refers to variations in a peptide sequence (of the multimer) wherein one or more amino acids may be substituted with other amino acids. The substitution is usually conservative, such as with amino acids that has similar properties. The variant(s) generally maintain a net charge of +1 to +11. The variant(s) are generally active and have good antimicrobial properties and low cytotoxicity.

A protected amino acid is an amino acid with one or more of its reactive groups modified with an inert molecule, to reduce and/or prevent chemical reactions of the reactive group.

DETAILED DESCRIPTION OF THE INVENTION

According to a first aspect, the present invention relates to an isolated multimer of defensin peptides of formula $(U)_n$, wherein U is a peptide comprising SEQ ID NO: 2 or a fragment or variant thereof and $n \geq 2$.

```
                                            SEQ ID NO: 2
GIINTLQKYYXRVRGGRXAVLSXLPKEEQIGKXSTRGRKXXRRZZ
```

X may comprise any amino acid; Z comprises any amino acid or may be absent. For example, Z may include but is not limited to lysine, ornithine or arginine. In particular, Z may be lysine.

According to another aspect, the present invention provides an isolated multimer comprising at least two units of a peptide U, wherein the peptide U comprises SEQ ID NO: 2 or a fragment or variant thereof.

The peptide U is repeated in the multimer. In particular, the repeating peptides U are linked together covalently. The peptides U may be linked together through at least one amino acid B. B may comprise an amino acid having at least two amine groups. For example, B may include but is not limited to lysine, ornithine or arginine.

The repeating unit or the peptide U in any multimer according to the present invention may be any peptide described in WO 2007/126392.

The peptide U may include peptide fragments derived from SEQ ID NO: 2. The fragments may be fragments of any length derived from SEQ ID NO: 2. In particular, the peptide U may comprise SEQ ID NO: 3 or fragment or variant thereof.

```
                                            SEQ ID NO: 3
GIINTLQKYYXRVRGGRXAVLSXLPKEEQIGKXSTRGRKXXRR
X comprises any amino acid.
```

The peptide U of the multimer may have a charge of +1 to +11.

Further, the peptide U may further comprise any one of SEQ ID NOs: 4 to 58 or fragment or variant thereof.

```
(38 aa peptide derived from hBD3 C terminus)
                                            SEQ ID NO: 4
KYYXRVRGGRXAVLSXLPKEEQIGKXSTRGRKXXRRZZ
X comprises any amino acid; Z comprises any amino acid or may be absent.

(36 aa peptide derived from hBD3 C terminus)
                                            SEQ ID NO: 5
YXRVRGGRXAVLSXLPKEEQIGKXSTRGRKXXRRZZ
X comprises any amino acid; Z comprises any amino acid or may be absent.

(40 aa peptide derived from hBD3 C terminus)
                                            SEQ ID NO: 6
LQKYYXRVRGGRXAVLSXLPKEEQIGKXSTRGRKXXRRZZ
X comprises any amino acid; Z comprises any amino acid or may be absent.

(29 aa peptide derived from hBD3 C terminus)
                                            SEQ ID NO: 7
RXAVLSXLPKEEQIGKXSTRGRKXXRRZZ
X comprises any amino acid; Z comprises any amino acid or may be absent.

SEQ ID NO: 8
KEEQIGKXSTRGRKXXRRZZ (20 aa peptide derived from hBD3 C terminus)
X comprises any amino acid; Z comprises any amino acid or may be absent.
```

-continued

SEQ ID NO: 9
KXSTRGRKXXRRZZ (14 aa peptide derived from hBD3 C terminus)
X comprises any amino acid; Z comprises any amino acid or may be absent.

SEQ ID NO: 10 (19 aa peptide derived from hBD3 aa 8-26)
KYYXRVRGGRXAVLSXLPK
X comprises any amino acid SEQ ID NO: 11
GIINTLQKYYXRVRGGR (17 aa peptide derived from hBD3 N-terminus)
X comprises any amino acid (full length hBD3 derived peptide, C replaced with W)
SEQ ID NO: 12
GIINTLQKYYWRVRGGRWAVLSWLPKEEQIGKWSTRGRKWWRRZZ
Z comprises any amino acid or may be absent.

(full length hBD3 derived peptide, C replaced F)
SEQ ID NO: 13
GIINTLQKYYFRVRGGRFAVLSFLPKEEQIGKFSTRGRKFFRRZZ
Z comprises any amino acid or may be absent.

(full length hBD3 derived peptide, C replaced Y)
SEQ ID NO: 14
GIINTLQKYYYRVRGGRYAVLSYLPKEEQIGKYSTRGRKYYRRZZ
Z comprises any amino acid or may be absent.

(full length hBD3 derived peptide, C replaced with S)
SEQ ID NO: 15
GIINTLQKYYSRVRGGRSAVLSSLPKEEQIGKSSTRGRKSSRRZZ
Z comprises any amino acid or may be absent.

(full length hBD3 derived peptide, C replaced with A)
SEQ ID NO: 16
GIINTLQKYYARVRGGRAAVLSALPKEEQIGKASTRGRKAARRZZ
Z comprises any amino acid or may be absent.

(full length hBD3 derived peptide, C replaced with C(Acm)
SEQ ID NO: 17
GIINTLQKYYC(Acm)RVRGGRC(Acm)C(Acm)VLSALPKEEQIGKC(Acm)STR
GRKC(Acm)C(Acm)RRZZ
Z comprises any amino acid or may be absent.

(full length hBD3 derived peptide, C replaced with C(But)
SEQ ID NO: 18
GIINTLQKYYC(But)RVRGGRC(But)C(But)VLSALPKEEQIGKC(But)STRGRK
C(But)C(But)RRZZ
Z comprises any amino acid or may be absent.

(full length hBD3 derived peptide, C replaced with C(t-Buthio)
SEQ ID NO: 19
GIINTLQKYYC(t-Buthio)RVRGGRC(t-Buthio)C(t-Buthio)VLSALPKEEQIGKC(t-
Buthio)STRGRKC(t-Buthio)C(t-Buthio)RRZZ
Z comprises any amino acid or may be absent (full length hBD3 derived peptide, C replaced with C(Bzl)
SEQ ID NO: 20
GIINTLQKYYC(Bzl)RVRGGRC(Bzl)C(Bzl)VLSALPKEEQIGKC(Bzl)STRGRKC
(Bzl)C(Bzl)RRZZ
Z comprises any amino acid or may be absent (full length hBD3 derived peptide, C replaced with C(4-MeBzl)
SEQ ID NO: 21
GIINTLQKYYC(4-MeBzl)RVRGGRC(4-MeBzl)C(4-
MeBzl)VLSALPKEEQIGKC(4-MeBzl)STRGRKC(4-MeBzl)C(4-MeBzl)RRZZ
Z comprises any amino acid or may be absent.

(full length hBD3 derived peptide, C replaced with C(4-MeOBzl)
SEQ ID NO: 22
GIINTLQKYYC(4-MeOBzl)RVRGGRC(4-MeOBzl)C(4-
MeOBzl)VLSALPKEEQIGKC(4-MeOBzl)STRGRKC(4-MeOBzl)C(4-
MeOBzl)RRZZ
Z comprises any amino acid or may be absent.

(full length hBD3 derived peptide, C replaced with C(Mmt)
SEQ ID NO: 23
GIINTLQKYYC(Mmt)RVRGGRC(Mmt)C(Mmt)VLSALPKEEQIGKC(Mmt)STRG
RKC(Mmt)C(Mmt)RRZZ
Z comprises any amino acid or may be absent.

-continued (full length hBD3 derived peptide, C replaced with modified C
SEQ ID NO: 24
GIINTLQKYYXRVRGGRXXVLSALPKEEQIGKXSTRGRKXXRRZZ
X comprises C(Acm), C(But), C(t-Buthio), C(Bzl), C(4-MeBzl), C(4-MeOBzl) or
C(Mmt); Z comprises any amino acid or may be absent (hBD3 derived 10 aa C-terminus fragment, C replaced with
any amino acid X)
SEQ ID NO: 25
RGRKXXRRZZ
X comprises any amino acid; Z comprises any amino acid or may be absent.

(hBD3 derived 10 aa C-terminus fragment, C replaced with W)
SEQ ID NO: 26
RGRKWWRRZZ
Z comprises any amino acid or may be absent.

(hBD3 derived 10 aa C-terminus fragment, C replaced with F)
SEQ ID NO: 27
RGRKFFRRZZ
Z comprises any amino acid or may be absent.

(hBD3 derived 10 aa C-terminus fragment, C replaced with Y)
SEQ ID NO: 28
RGRKYYRRZZ
Z comprises any amino acid or may be absent.

(hBD3 derived 10 aa C-terminus fragment, C replaced with L)
SEQ ID NO: 29
RGRKLLRRZZ
Z comprises any amino acid or may be absent.

(hBD3 derived 10 aa C-terminus fragment, C replaced with I)
SEQ ID NO: 30
RGRKIIRRZZ
Z comprises any amino acid or may be absent.

(hBD3 derived 10 aa C-terminus fragment, C replaced with H)
SEQ ID NO: 31
RGRKHHRRZZ
Z comprises any amino acid or may be absent.

(hBD3 derived 10 aa C-terminus fragment, C replaced with
C(Acm), C(But), C(t-Buthio), C(Bzl), C(4-MeBzl), C(4-MeOBzl) or C(Mmt)..
SEQ ID NO: 32
RGRKXXRRZZ
X comprises C(Acm), C(But), C(t-Buthio), C(Bzl), C(4-MeBzl), C(4-MeOBzl) or
C(Mmt); Z comprises any amino acid or may be absent.

(hBD3 derived 10 aa C-terminus fragment, C replaced with V)
SEQ ID NO: 33
RGRKVVRRZZ
Z comprises any amino acid or may be absent.

(hBD3 derived 10 aa C terminus peptide)
SEQ ID NO: 34
RGRKCCRRZZ
Z comprises any amino acid or may be absent.

(hBD3 derived 10 aa C-terminus peptide, C replaced with
C(Acm), C(But), C(t-Buthio), C(Bzl), C(4-MeBzl), C(4-MeOBzl) or C(Mmt).
SEQ ID NO: 35
RGRKXXRRKK
X comprises C(Acm), C(But), C(t-Buthio), C(Bzl), C(4-MeBzl), C(4-MeOBzl) or
C(Mmt).

(hBD3 derived C-terminus peptide excluding terminal KK, C
replaced with any amino acid)
SEQ ID NO: 36
RGRKXXRR (hBD3 derived C-terminus peptide excluding terminal KK, C
replaced with W, W2-8AA)
SEQ ID NO: 37
RGRKWWRR (hBD3 derived C-terminus peptide excluding terminal KK, C
replaced with F)
SEQ ID NO: 38
RGRKFFRR -continued (hBD3 derived C-terminus peptide excluding terminal KK, C
replaced with Y, Y2-8AA)
RGRKYYRR
SEQ ID NO: 39

(hBD3 derived C-terminus peptide excluding terminal KK, C
replaced with L)
RGRKLLRR
SEQ ID NO: 40

(hBD3 derived C-terminus peptide excluding terminal KK, C
replaced with I)
RGRKIIRR
SEQ ID NO: 41

(hBD3 derived C-terminus peptide excluding terminal KK, C
replaced with H)
RGRKHHRR
SEQ ID NO: 42

(hBD3 derived C-terminus peptide excluding terminal KK, C
replaced with C(Acm), C(But), C(t-Buthio), C(Bzl), C(4-MeBzl), C(4-MeOBzl)
or C(Mmt).
RGRKCXXRR
X comprises C(Acm), C(But), C(t-Buthio), C(Bzl), C(4-MeBzl), C(4-MeOBzl) or
C(Mmt).
SEQ ID NO: 43

(hBD3 derived C-terminus peptide excluding terminal KK, C
replaced with V, V2-8AA)
RGRKVVRR
SEQ ID NO: 44

(V2 monomer)

RGRKVVRRKK
SEQ ID NO: 45

(V4 monomer, V4-10 AA)

RGRKVVRRVV
SEQ ID NO: 46

(Y4 monomer, Y4-10 AA)

RGRKYYRRYY
SEQ ID NO: 47

(W4 monomer, W4-10 AA)

RGRKWWRRWW
SEQ ID NO: 48

(V3 monomer)

RVRKVVRR
SEQ ID NO: 49

(V2R monomer)

RRRKVVRR
SEQ ID NO: 50

(V2D monomer)

RDRKVVRR
SEQ ID NO: 51

(E2 monomer)

RGRKEERR
SEQ ID NO: 52

(K2 monomer)

RGRKKKRR
SEQ ID NO: 53

RRRRRRRRRR
SEQ ID NO: 54

VVVV
SEQ ID NO: 55

-continued

YYYY

RRVVKRGR SEQ ID NO: 56

SEQ ID NO: 57

RRVVKRGRK SEQ ID NO: 58

According to another aspect, the invention relates to an isolated multimer of formula $(U)_n B_m Z_j$, wherein U comprises SEQ ID NO: 3 or a fragment or variant thereof, B comprises an amino acid having at least two amine groups, Z comprises any amino acid, $n \geq 2$, $m \geq 1$ and $j \geq 0$. In particular, each B may include but is not limited to lysine, ornithine or arginine.

According to one aspect of the invention, the B and Z in $(U)_n B_m Z_j$ may both comprise lysine (K) and the formula may be expressed as $(U)_n K_m K_j$. According to a further aspect, m may also equal the number n−1 and j may equal to 1 and the formula of the multimer may be expressed as $(U)_n K_{n-1} K$ (or $(UK)_n$. The peptide U in $(U)_n K_m K_j$ or $(U)_n K_{n-1} K$ may comprise SEQ ID NO: 3 or a fragment or variant thereof.

The peptide U in the formula $(U)_n B_m Z_j$, $(U)_n K_m K_j$ or $(U)_n K_{n-1} K$ may comprise SEQ ID NO: 3 or a fragment or variant thereof, such as RGRKXXRR (SEQ ID NO: 36) or any one of SEQ ID NOs: 37-44.

For example, if m=n−1, j=1, B=Z=K, U comprises SEQ ID NO: 44, the multimer has the formula (SEQ ID NO: 44)$_n$ $K_{n-1}K$. If n=2, the multimer has the formula (SEQ ID NO: 44)$_2$KK.

The multimer(s) of the invention may be linear or branched. If the multimer $(U)_n$ is linear, the peptide U repeated n times may comprise SEQ ID NO: 2 or any fragment or variant of SEQ ID NO: 2, such as any one of SEQ ID NOs: 3-58. For example, the multimer may comprise (SEQ ID NO: 35)$_n$, (SEQ ID NO: 36)$_n$ or (SEQ ID NO: 45)$_n$.

For a branched multimer, for example the multimer $(U)_n B_m Z_j$, the multimer may be branched at the terminal $B_m Z_j$ residues.

The multimer may comprise any number of repeating units. For example, the multimer may comprise 2 to 10, 2 to 20, 2 to 30 repeating subunits. In addition, the multimer may be a dimer, trimer, tetramer, pentamer, hexamer, heptamer, octamer, nonamer and decamer.

For example, for a branched dimer of formula (SEQ ID NO: 36)$_2$BZ, the branched dimer may comprise the structure:

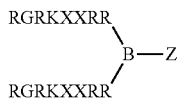

As an alternative, Z may be absent and the dimer may have the structure:

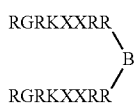

In particular, for any of the multimer according to the invention, X may be V. The V2 monomer has the sequence RGRKVVRR (SEQ ID NO: 44).

According to a further aspect, the invention also relates to a method of preparing at least one multimer of formula: $(U)_n K_m Z_j$, wherein U comprises SEQ ID NO: 3 or a fragment or variant thereof, Z comprises any amino acid and $n \geq 2$, $m \geq 1$ and j=1.

(i) providing at least one solid phase;
(ii) coupling at least a first amino acid residue Z to the solid phase;
(iii) linking at least one protected K residue to the coupled first amino acid residue;
(iv) removing the protecting group(s) from the linked K residue(s)
(v) providing additional chain extension by linking protected amino acid residues, according to the sequence of the peptide U in order from the C-terminus to the N-terminus, wherein after each linking, the protecting groups are removed for the next linking; and
(vi) terminating the linking of amino acid residues depending on the number of residues to be added.

The amino acid Z first coupled to the solid phase may be any amino acid. For example, Z may include but is not limited to lysine, ornithine or arginine.

Following completion of the synthesis of the multimer, the multimer may be released from the solid phase.

For example, performing the above steps for the peptide sequence RGRKKXXRR (SEQ ID NO: 36) will produce the following dimer. The lysine (K) residue in bold italics shows the positions which Lys(Fmoc) was incorporated during the synthesis.

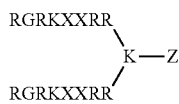

In the synthesis method, the Z and lysine residues are shared between the monomer units.

In particular, when X is V and Z is K, the dimer below is produced. This dimer is the V2 dimer, (SEQ ID NO: 44)$_2$KK.

The method may be extended to produce further multimers. For example, the extended method to produce further multimers further comprises, after step (iv)

(iv)(a) linking further protected lysine residues to the linked second lysine residue(s);
(iv)(b) removing the protecting group(s) from the lysine residues from (iv)(a);
(iv)(c) repeating step (iv)(a) and (iv)(b), or
(iv)(d) proceeding to step (v) and (vi).

This extended method will produce multimers increasing in multiples of two from the previous multimer. The multimers formed from the extended method will be four, eight, sixteen, thirty-two, sixty-four and so on. Repeating the additional steps of the extended method once produces a tetramer, as shown below. If X is V and B and Z are K, then the tetramer is known as the V2-tetramer. The repeated unit in the V2 tetramer is RGRKVVRR (SEQ ID NO: 44).

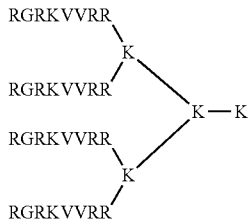

Further, repeating the additional steps of the extended method twice will produce an octamer. The multimer(s) of the invention may exclude the terminal K residue.

The multimers prepared as described above are homogeneous multimers (homo-multimers), such that a peptide monomeric unit is repeated in the multimers. The peptide multimers of the invention may be homo-dimers, homo-tetramers or other homo-multimers.

Further, the method of preparation may be extended to prepare heterogenous multimers, such that the peptide units in the multimers are different. When preparing the homo-multimers, the protected amino acid B have at least two side chains protected by the same protecting group. However, for preparing a heterogeneous multimer, for example, a heterogeneous dimer, a differentially protected amino acid C may be used, wherein the side groups available for chain extension are protected by at least two different protection groups. In this case, a first protection group may be removed to allow peptide chain extension from at least a first reactive side group. After the first peptide chain extension(s) are completed, the other protection group may be removed to allow subsequent chain extension from at least a second reactive side group. In this way, the first peptide chain and the second peptide chain may have different amino acid sequences.

According to another aspect, the invention relates to a method of preparing a peptide multimer of formula $[(U^1)(U^2)]_{n/2}(C)_{n/2}B_mZ$ wherein each of $U^1$ and $U^2$ comprises a peptide with $U^1 \neq U^2$, $n=2^x$, where x=0 or a positive integer, m=1 or 0; comprising the steps of:
(i) providing at least one solid phase;
(ii) coupling at least a first amino acid Z to the solid phase;
(iii) optionally linking at least one amino acid B to the coupled Z;
(iii) linking at least one protected amino acid C to Z or B; wherein C comprises at least two differentially protected groups;
(iv) removing a first protecting group from the linked amino acid C to expose a first reactive side chain;
(v) providing chain extension of a first peptide $U^1$ to the first reactive side chain of C;
(vi) removing a second protecting group from the linked B amino acid to expose at least a second reactive side chain; and
(viii) providing chain extension of a second peptide $U^2$ to the second reactive side chain of C.

A heterogeneous peptide multimer may thus be prepared.

If the optional step (ii) is omitted, a hetero-dimer is formed. A hetero-tetramer may be prepared if the optional step (ii) is performed once. Other heterogeneous multimers may be prepared by repeating step (ii) accordingly.

According to another aspect, the invention relates to an isolated peptide multimer of formula $[(U^1)(U^2)]_{n/2}(C)_{n/2}B_mZ$, wherein $U^1$ and $U^2$ comprises a peptide sequence with $U^1 \neq U^2$, C and B each comprises an amino acid with at least two amine groups, Z comprises any amino acid, n=2', where x=0 or a positive integer, m=1 or 0.

Each of C, B and Z may include but is not limited to lysine (K), ornithine or arginine (R).

In particular, $U^1$ or $U^2$ may each be a peptide comprising SEQ ID NO: 2 or a fragment or variant thereof.

$U^1$ may comprise but is not limited to any one of SEQ ID NOs: 1 to 58.

$U^2$ may comprise but is not limited any one of SEQ ID NOs: 1 to 58.

If n=2 and m=1, the multimer is a heterogenous dimer of formula $[(U^1)(U^2)]CZ$.

For example, $U^1$ may comprise RGRKVVRR (SEQ ID NO: 44) and $U^2$ may comprise RGRKVVRRVV (SEQ ID NO: 46), C and Z are K, m=0, n=2. The structure of the heterogeneous dimer comprises:

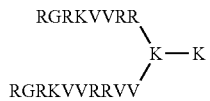

For example $U^1$ may comprise RRRRRRRRRR (SEQ ID NO: 54) and $U^2$ may comprise VVVV (SEQ ID NO: 55), C and Z are K, m=0, n=2. The structure of the heterogeneous dimer comprises:

For example $U^1$ may comprise RRRRRRRRRR (SEQ ID NO: 54) and $U^2$ may comprise YYYY (SEQ ID NO: 56), C and Z are K, m=0, n=2. The structure of the heterogeneous dimer comprises:

If n=4 and m=1, the heterogenous multimer is a heterogeneous tetramer. A heteromer may be of formula $[(U^1)(U^2)]_2(C)_2B_1Z$.

The method of the invention may also be extended to synthesise other multimeric peptides, such as trimers. Both homo-trimers and hetero-trimers may be synthesised.

A method of preparing a peptide trimer of formula $U^3U^2CU^1Z$, wherein $U^1$, $U^2$ and $U^3$ each comprises a peptide, C comprises an amino acid comprising at least two amine groups and Z comprises any amino acid, the method comprising the steps of:
(i) providing at least one solid phase;
(ii) couping at least a first amino acid Z to the solid phase; and
(iii) providing chain extension of peptide $U^1$ to Z;
wherein, (A) the peptide trimer is a heterogeneous peptide of formula $U^3U^2(C)U^1Z$, the method further comprises:
(iv) linking a differentially protected amino acid C to an amino acid of peptide $U^1$;

(v) removing a first protecting group from the linked amino acid C;
(vi) providing for chain extension of peptide U² to amino acid C;
(vii) removing a second protecting group from the linked amino acid C; and
(viii) providing for chain extension of peptide U³ to amino acid C;

(B) U²=U³=U¹, C=B, and the peptide trimer comprises formula $(U^1)_2BU^1Z$, the method further comprises:
(iv) linking a protected amino acid B to an amino acid of peptide U¹;
(v) removing the protecting groups from the linked amino acid B; and
(vi) providing for chain extension of two peptides U¹ to the amino acid B; or (C) U²=U³≠U¹, C=B, and the peptide comprises formula $(U^2)_2B(U^1)Z$, the method further comprises:
(iv) linking a protected amino acid B to an amino acid of peptide U¹;
(v) removing the protecting groups from the linked amino acid B; and
(vi) providing for chain extension of at least two units of peptide U² to amino acid B.

In the case of (A) and (C) above, a heterogenous peptide trimer may thus be prepared. In the case of (B) above, a homogeneous peptide trimer may thus be prepared.

According to another aspect, the invention relates to an isolated peptide trimer of formula $U^3U^2CU^1Z$; wherein U¹, U², U³ each comprises a peptide sequence; C comprises an amino acid comprising at least two amine groups and Z comprises any amino acid. In particular, the peptide is branced at amino acid C.

The structure of the isolated peptide trimer comprises:

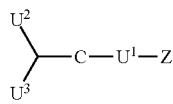

Each of C, B and Z may include but is not limited to lysine (K), ornithine or arginine (R).

In particular, U¹, U² or U³ may each comprise SEQ ID NO: 2 or or a fragment or variant thereof.

For example, U¹, U² or U³ may each comprise any one of SEQ ID NOs: 1 to 58. For a heterogeneous peptide trimer, two of the peptides may comprise the same sequence with the third peptide of a different sequence.

For the heterogeneous peptide trimer, $U^3U^2CU^1Z$, U¹, U² and U³ may be but need not be different peptide sequences. For example, U¹ and U² may comprise the same sequence while U³ may comprise a different sequence. Alternatively, U¹ and U³ may comprise the same sequence with U² having the same sequence.

If U²=U³≠U¹ and C=B, the peptide is of formula $(U^2)_2BU^ZZ$.

If U¹=U³≠U², the peptide is of formula $U^1U^2CU^1Z$.
If U¹=U²≠U³, the peptide is of formula $U^3U^1CU^1Z$.
However, if U¹=U²=U³ and C=B, the peptide is of formula $(U^1)_2 BU^1Z$ (homeogeneous peptide trimer).

An example of a heterogeneous peptide trimer with and its synthesis is illustrated in FIG. 8 and described in Example 10.

Accordingly, the invention relates to an isolated peptide trimer of formula $U^3U^2KU^1K$; wherein U¹ comprises RRVVKRGR (SEQ ID NO: 57) and U² comprises RGRKVVRR (SEQ ID NO: 44) and U³ comprises RGRKVVRRVV (SEQ ID NO: 46). This heterogeneous trimer is the V2V2V4-heterotrimerm and has the structure:

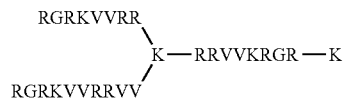

The multimers of the present invention possess antimicrobial properties. Accordingly, the multimers may be used for inhibiting and/or reducing the growth of microorganisms.

The present invention also provides a method of inhibiting and/or reducing the growth of microorganisms comprising contacting the microorganism with at least one multimer of the invention.

The present invention also provides a method of treating at least one microbial infection comprising administering to a subject at least one multimer of the invention. The invention further provides inhibiting and/or reducing the growth of at least one microorganism in a subject comprising administering to the subject at least one multimer of the invention.

The microorganism may be a virus, fungus or bacteria.

Accordingly, the present invention also relates to the use of a multimer according to any aspect of the invention in the manufacture of an antimicrobial composition. The antimicrobial composition may be used for inhibiting and/or reducing the growth of at least one microorganism, for example, in a subject.

The present invention also includes the use of a multimer according to any aspect of the invention in the manufacture of a medicament for treating at least one microbial infection.

Accordingly, the multimer(s) of the invention may be formulated into antimicrobial compositions and/or pharmaceutical compositions. The antimicrobial and/or pharmaceutical compositions may be formulated for topical, oral, parenteral administration or for administration by inhalation. The multimer(s) of the invention may also be formulated in eye drop composition(s) and/or solution(s) and/or contact lens solution(s).

The multimer(s) of the invention may also be formulated into compositions for coating devices. The devices include medical devices such as but not limited to a catheter, a needle, a sheath, a stent or a dressing.

The invention further includes kit(s) comprising at least one multimer according to the invention, at least one antimicrobial composition and/or pharmaceutical composition comprising at least one multimer according to the invention.

Having now generally described the invention, the same will be more readily understood through reference to the following examples which are provided by way of illustration, and are not intended to be limiting of the present invention.

EXAMPLES

Standard molecular biology techniques known in the art and not specifically described were generally followed as described in Sambrook and Russel, Molecular Cloning: A Laboratory Manual, Cold Springs Harbor Laboratory, New York (2001).

Example 1

Method for Solid-Phase Peptide Synthesis (SPPS) of Multimers (A) Synthesis of homogeneous dimer The method for the synthesis of the peptides is adapted from Krajewski et al., (2004). Fluorenylmethoxycarbonyl (Fmoc)-protected L-amino acids and resin were purchased from Advanced Automated Peptide Protein TECHNOLOGIES, AAPPTEC) (KY, US) and used with the following side-chain protective groups: Lys(Fmoc) was incorporated only at second residue from C-terminus for synthesis of dimers, Arg(pbf), Lys(Boc), Tyr(But), Trp(Boc) and Fmoc-Lys(Boc)-Wang resin (substitution 0.72 mmol/g). Syntheses of dimers were carried out on Apex 396 (Advanced ChemTech) by Fmoc chemistry.

Commercially available Fmoc-Boc-Lys-Wang resin was used as the starting point. Alternatively, coupling of the first amino acid to the Wang resin was carried out with 0.5 M DIC (N,N'-diisopropylcarbodiimide). Subsequent coupling reactions (or acylation) were carried out with 0.5M HBTU/0.5M HOBT/2M DIEA in NMP. As an alternative, the coupling reactions may also be carried out with HBTU-HOBT in DMF at a synthesis scale of 0.08 mmol. Fmoc deprotection was carried out with 20% piperidine in DMF.

The resins were treated with 90% TFA (trifluortacetic acid), 5.0% phenol, 1.5% water, 1.0% TIS (triisoproply silane), 2.5% EDT (ethane diol) to release the multimer from the resins. Alternatively, the resulting peptidyl resins may be treated with a freshly prepared mixture of TFA/TIS/phenol/Thionisole/water (90/1/2.5/5/1.5, the ratio of volume percent) for 2-3 h at room temperature.

The crude peptides were then precipitated by filtration into ice-cold diethyl ether, separated by centrifugation, washed three times with ice-cold ether and dried by automated evaporation of ether and other remaining or residual solvents in crude solid products in fume hood or dried under vacuum at room temperature. The precipitate dried directly from the ether resulted in a TFA (trifluoroacetic acid) salt. TFA salts may affect the pH of peptide solutions or the viability of cells in culture. Lyophilization from 2 ml 2% acetic acid replaces the TFA salt with an acetic salt, which allows easier handling the other peptides and removes trace amounts of scavengers.

Figure 2:
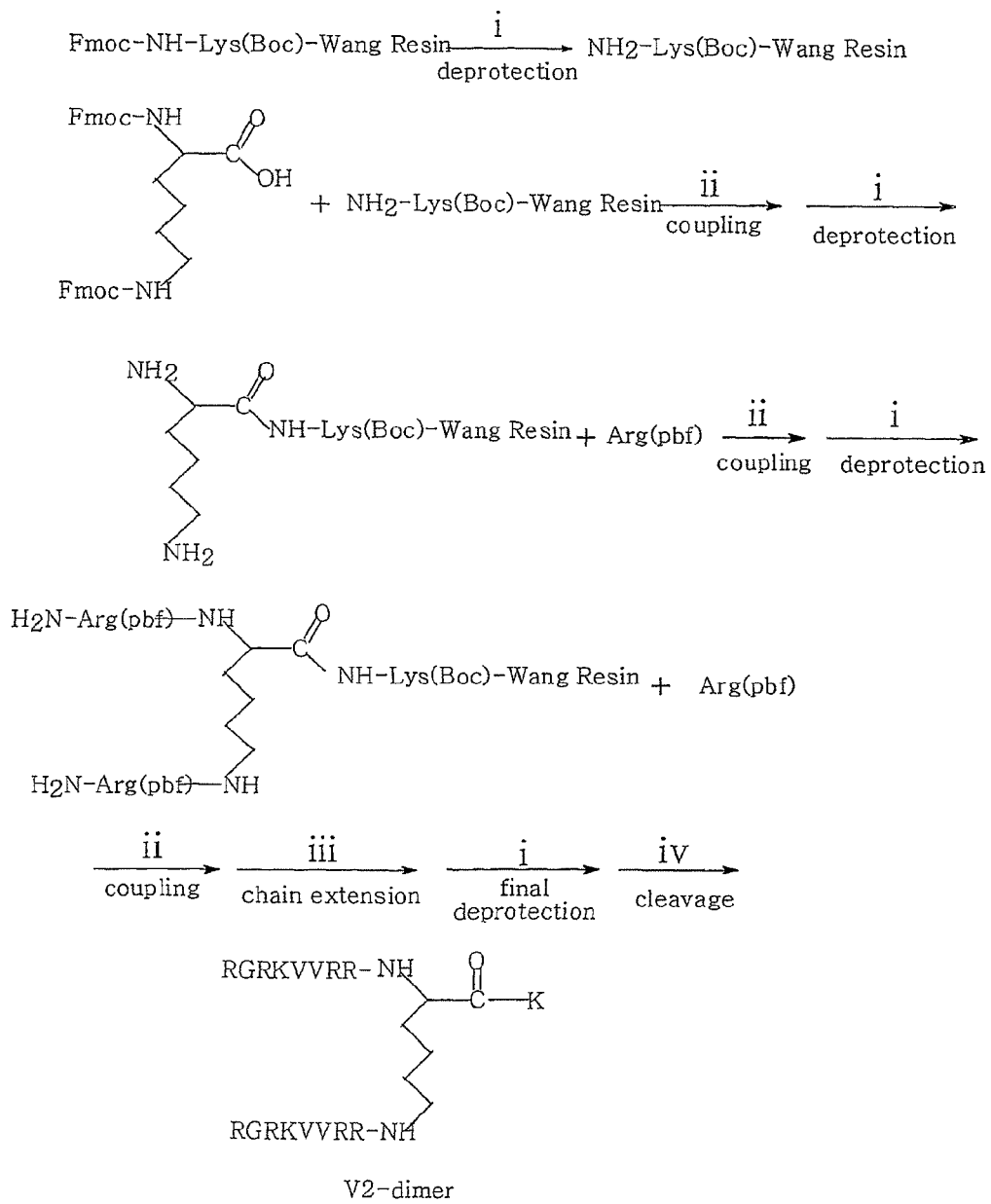
FIG. 2 illustrates the synthesis of the V2 dimer by solid-phase peptide synthesis (SPPS).

The scheme of the synthesis method is illustrated in FIG. 2.

High yields of crude dimer and purified dimer may be obtained from this SPPS method. For example, yields of crude and purified V2-dimer are 90 and 27%, respectively. Further, 50 mg purified V2-dimer may be obtained based on 0.08 mmol synthesis scale.

The method described is an example of the synthesis method but modifications to the method may be made. For example, any method for the protection and deprotection of the amino acid residues may be used in the SPPS method.

(B) Synthesis of Homogeneous Tetramer

The synthesis method may be extended to the synthesis of a homogeneous tetramer as illustrated in FIG. 9.

Following deprotection of the Fmoc-Lys linked to the immobilised $NH_2$-Lys(Boc), two Fmoc-Lys residues were then linked to the Lys. Further amino acids chain extension were then perfomed to produce a homogeneous tetramer (V2 tetramer) as illustrated. The conditions for the deprotecion (step i), coupling (step ii) and chain extension were the same as for the preparation of the homogeneous dimer.

(C) Synthesis of Heterogeneous Dimer

For the synthesis of a heterogeneous dimer as illustrated in FIG. 7, the differentially protected amino acid Fmoc-Lys (Aloc)-OH was used as the branched site to prepare a heterodimer. The Fmoc and Aloc groups have different reactivity with Aloc being stable under the basic conditions used to remove Fmoc.

The deprotection of the immobilised Fmoc-NH-Lys(Boc)-Wang resin was performed as described above.

As illustrated in FIG. 7, Fmoc-Lys(Aloc)-OH was then linked to the lysine residue attached to the Wang resin (coupling step ii). Only the Fmoc group of Fmoc-Lys(Aloc) was removed (Fmoc deprotection) and extension of the first chain was performed with (step iii). When all the amino acid residues in the first chain had been linked, (i.e. the first chain completed), the Aloc group on the Lys(Aloc) was removed (Aloc deprotection) using a Palladium catalyst and the second chain extension was performed. When all the amino acid residues in the second chain had been linked (i.e. second chain also completed), the product was released by acid cleavage. Any remaining protecting groups used to protect reactive groups of the amino acid residues as appropriate (eg Boc, pbf, Mtr) during the synthesis were then removed.

(D) Synthesis of Heterogeneous Peptide Trimer

An example of the synthesis of a heterogeneous peptide trimer is illustrated in FIG. 8. The first extension to the immobilised lysine (K) residue is a first peptide ($U^1$) of RGRKV-VRR (SEQ ID NO: 57). Subsequently, an Fmoc-Lys(Aloc)-OH is linked to the R residue at the N terminus of the peptide RGRKVVRR. The Fmoc group is then removed and a second peptide ($U^2$) of RGRKVVRR (SEQ ID NO: 44) is added by chain extension to the first amine group of the Lys(Aloc) residue. Following the second chain extension, the Aloc group is removed and a third peptide ($U^3$) of RGRKVVR-RVV (SEQ ID NO: 46) is added by chain extension to the second amine group of the Lys residue.

Alternatively, Fmoc-Lys(Fmoc)-OH may also be added after the extension of the first peptide $U^1$ is completed. A peptide $U^2$ may be extended in duplicate to form the heterogenous trimer $U^2U^2(K)U^1K$.

For a homogeneous peptide trimer, Fmoc-Lys(Fmoc)-OH may be used after the extension of the peptide U is completed. The same peptide U may then be extended in duplicate simultaneously to form the homogeneous trimer.

Example 2

Antimicrobial Assay

The method for testing antimicrobial activity of antimicrobial peptides used an absolute killing procedure as described below.

Preparation of Test Organisms

The test organisms were either reference cultures obtained from American Type Culture Collection (ATCC) or clinical isolates obtained from the Department of Pathology, Singapore General Hospital. All cultures used in the study were not more than 5 passages from the source.

The bacterial cultures were grown on Trypticase Soy Agar (TSA) slants, and the yeast culture on Sabouraud Dextrose Agar (SDA) slants at 35° C. for 16 hours. The organisms were harvested by centrifugation and washing twice in Phosphate buffer, pH 7.2 (United States Pharmacopeia, USP) at 20° C.

Test Organisms Used

The following organisms were used in the study:
1. *Bacillus cereus* ATCC 11778
2. *Candida albicans* ATCC 10231
3. Clinical *Pseudomonas aeruginosa* PAE230 DR4877/07. Source: Sputum 4. Clinical *Pseudomonas aeruginosa* PAE239 DM5790/07. Source: Wound
5. Clinical *Pseudomonas aeruginosa* PAE240 DU14476/07. Source: Urine
6. Clinical *Pseudomonas aeruginosa* PAE249 DM15013. Source: Wound
7. Clinical *Pseudomonas aeruginosa* 07DMO23257. Source: Eye
8. Clinical *Pseudomonas aeruginosa* 07DMO23376. Source: Eye
9. Clinical *Pseudomonas aeruginosa* 07DMO23155. Source: Eye
10. Clinical *Pseudomonas aeruginosa* 07DMO23104. Source: Eye
11. *Pseudomonas aeruginosa* ATCC 9027
12. *Pseudomonas aeruginosa* ATCC 27853
13. *Escherichia coli* ATCC25922
14. Clinical *Escherichia coli* DB16027 Source: Blood
15. Clinical *Escherichia coli* DU46381 R Source: Urine
16. Methicillin-resistant *Staphylococcus aureus* (MRSA) DM09808R Source: Eye
17. Clinical *Staphylococcus* aueus DM4001 Source: Eye
18. Clinical Candid albicans DF2672R Source: Urine
19. *Fusarium solani* ATCC 36031

Preparation of Test Solutions of Compounds

The freeze-dried antimicrobial compound was dissolved in purified water and distributed into screw-capped plastic tubes at a concentration of 1,000 micro-grams (µg) per ml. These served as stock solutions and were kept at −20° C.

On the day of conducting the test, one tube of the stock solution was defrosted and diluted in purified water to a concentration of 500 µg/ml. Thereafter, further dilutions were carried out in either USP Phosphate Buffer, pH 7.2 or other solutions (including but not limited to 10 mM sodium phosphate buffer, pH 7.4, 10 mM potassium buffer 7.2 or 155.2 mM NaCl), to the test concentrations required, normally ranging from 6.25 µg/ml to 50 µg/ml.

Ten micro-litres (µl) of the test organism of standardised concentration was inoculated into one ml of the compound test solution of specific test concentration to provide a final count of between $1 \times 10^5$ cfu/ml and $1 \times 10^6$ cfu/ml as far as possible. The inoculated test solutions were than incubated at 35° C. for 4 hours. The incubation temperature and time may be varied as required.

After incubation, the antimicrobial activity of the test solutions was inactivated by a 10-fold dilution in D/E Neutralising Broth (NB). Further dilutions were carried out in the NB, and plated out in TSA for bacteria, and SDA for yeast culture. The plates were incubated at 35° C. for 72 hours. The viable count of the survivor organisms was then determined.

As an inoculum control, the test organism was inoculated, parallel to the Test, into the buffer used in the preparation of the test solutions instead and incubated under the same condition as the Test. The viable count of the inoculum control was determined as for the Test.

The antimicrobial activity of the compound was expressed as log reduction calculated by subtracting the log number of colony forming units (cfu) of the test organism survivor after 4 hours' exposure time at 35° C. from the log number of cfu of the inoculum control of the test organism.

The method described above was used for Examples 3-7 and in particular, the method for gentamicin in Example 6 is similar except that gentamicin was substituted for the antimicrobial compound.

Example 3

Antimicrobial activity of V2 dimer against *P. aeruginosa* ATCC 9027

The antimicrobial properties of the V2 dimers were tested on *Pseudomonas aeruginosa* ATCC 9027.

The V2 dimer shows antimicrobial activity against *P. aeruginosa* ATCC 9027 in USP Phosphate buffer (prepared according to US Pharmacopeia Convention) at physiological pH 7.2. The antimicrobial activity was efficient, showing large reductions in the bacterial population. (See Table 1). The inoculating amount of bacteria was ~$10^7$ organisms and at 4 hours of contact time at 12.5 µg/ml of V2 dimer, the solution was almost sterilised.

TABLE 1

Antimicrobial activity against *P. aeruginsa* ATCC 9027 (Log Reduction) in USP Phosphate buffer pH 7.2 at 35° C.

| Diluent for dilution of sample from 100 ug/ml to test concentration | USP Phosphate Buffer pH 7.2 | USP Phosphate Buffer pH 7.2 | USP Phosphate Buffer pH 7.2 |
| --- | --- | --- | --- |
| Test Concentration ug/ml | 4 hrs | 4 hrs | 4 hrs |
| 25.0 | >6.54 | >6.38 | ND |
| 12.5 | >6.54 | >6.38 | ND |
| 6.25 | 2.82 | 1.84 | 3.04 |
| 3.125 | 0.59 | 0.22 | 0.69 |

The salt solution of the USP buffer used above is dilute compared to physiological conditions, and therefore the antimicrobial activity of the V2 dimer was also tested at physiological salt conditions using 10 mM phosphate buffer pH 7.2. The V2 dimer also maintained high antimicrobial activity against *P. aerugonisa* ATCC 9027 at physiological salt concentration (Table 2).

TABLE 2

Antimicrobial Activity against *Pseudomonas aeruginosa* ATCC 9027 (Log Reduction) in 10 mM Potassium Phosphate Buffer pH 7.2 at 35° C.

| Diluent for dilution of sample from 100 ug/ml to test concentration | 10 mM Potassium Phosphate Buffer |
| --- | --- |
| Test Concentration ug/ml | |
| 50.0 | 5.63 |
| 25.0 | 5.63 |
| 12.5 | 2.93 |
| 6.25 | 2.20 |
| 3.125 | 2.00 |

In addition, the antimicrobial activity of the V2 dimer was also assayed under high salt concentration of 155.2 mM NaCl. The results indicated that the V2 dimer at concentrations of 12.5 to 50 µg/ml had antimicrobial activity at high salt concentration.

TABLE 3

Antimicrobial Activity against *Pseudomonas aeruginosa* ATCC 9027 (Log Reduction) at 35° C.

| Diluent for dilution of sample from 100 ug/ml to test concentration | 155.2 mM NaCl | 155.2 mM NaCl | 155.2 mM NaCl |
|---|---|---|---|
| Test Concentration µg/ml | 4 hrs | 4 hrs | 4 hrs |
| 50.0 | ND | 5.23 | 2.82 |
| 25.0 | 2.82 | 2.78 | 1.71 |
| 12.5 | 1.71 | 2.14 | 0.78 |
| 6.25 | 0.78 | ND | ND |
| 3.125 | ND | ND | ND |

ND—not determined.

Example 4

Comparison of the V2 Dimer with hBD3 Derived Peptide Monomers 10 amino acid peptide monomers derived from hBD3 as described previously (WO 2007/126392) were also assayed for their activity against *P. aeruginosa* ATCC 9027.

The antimicrobial properties of the monomers of V2, L2, C2, F2 and H2 in USP phosphate buffer were studied and shown in Table 4.

TABLE 4

Antimicrobial Activity of 10 amino acid peptide monomers against *Pseudomonas aeruginosa* ATCC 9027 (Log Reduction) at 35° C.

| Concentration | V2 | V2 | L2 | C2 | F2 | H2 |
|---|---|---|---|---|---|---|
| ug/ml | 4 hrs | 6 hrs | 4 hrs | 4 hrs | 4 hrs | 4 hrs |
| 200.00 | ND | ND | ND | 0.41 | 0.33 | 0.29 |
| 100.00 | ND | ND | 0.78 | 0.57 | 0.61 | 0.62 |
| 50.00 | 3.97 | 5.62 | 1.15 | 0.63 | 0.87 | ND |
| 25.00 | 3.33 | ND | 1.09 | ND | ND | ND |
| 12.5 | 3.23 | ND | 0.95 | ND | ND | ND |
| 6.25 | 3.80 | ND | 1.17 | ND | ND | ND |
| 3.125 | 0.50 | ND | 1.01 | ND | ND | ND |
| 1.558 | 0.35 | ND | 0.89 | ND | ND | ND |

ND—not determined
Note:
0.5 log reduction equals to 68% bacteria being killed; 1 log reduction equals to 90% bacteria being killed; 2 log reduction equals to 99% bacteria being killed; 3 log reduction equals to 99.9% bacteria being killed.

Comparing the results of the V2 dimer in Table 1 to the V2 monomer in Table 4 the V2 dimer shows a much higher efficiency in killing than the V2 monomer. The V2 dimer showed a >6 log reduction (Table 1) at a concentration of 12.5 µg/ml at 4 hours compared to the V2 monomer which shows a 3.23 log reduction at 12.5 µg/ml and only a 3.97 log reduction at 50 µg/ml (Table 4).

Example 5

Antimicrobial Activity of V2 Dimer Against Clinical Isolates of *P. aeruginosa*

The antimicrobial activity of the V2 dimer was also tested against several clinical isolates of *P. aeruginosa* from the sputum, wound, urine and the eye. The V2 dimer also showed antimicrobial activity against these clinical isolates (See Tables 5-8), suggesting that the V2 primer may be effectively used against actual clinical specimens.

TABLE 5

Antimicrobial activity of V2 dimer against clinical strains of *P. aeruginosa* (Log Reduction) isolated from sputum at 35° C.

| Diluent for dilution of sample from 100 ug/ml to test concentration | USP Phosphate Buffer pH 7.2 | USP Phosphate Buffer pH 7.2 | USP Phosphate Buffer pH 7.2 |
|---|---|---|---|
| Type of Clinical *Pseudomonas aeruginosa* | PA1-PAE 230 DR4877/07 Source: Sputum | PA1-PAE 230 DR4877/07 Source: Sputum | PA1-PAE 230 DR4877/07 Source: Sputum |
| Test Concentration ug/ml | 4 hrs | 4 hrs | 4 hrs |
| 50.0 | 4.53 | >5.52 | >5.49 |
| 25.0 | 4.44 | 5.22 | >5.49 |
| 12.5 | 3.02 | 3.65 | 5.07 |
| 6.25 | 2.21 | 2.41 | 3.12 |
| 3.125 | 1.49 | 1.99 | 2.41 |

TABLE 6

Antimicrobial activity of V2 dimer against clinical strains of *P. aeruginosa* (Log Reduction) isolated from wound at 35° C.

(A) Data for *P. aeruginosa* PAE239 DM5790/07

| Diluent for dilution of sample from 100 ug/ml to test concentration | USP Phosphate Buffer pH 7.2 | USP Phosphate Buffer pH 7.2 | USP Phosphate Buffer pH 7.2 |
|---|---|---|---|
| Type of Clinical *Pseudomonas aeruginosa* | PA2-PAE 239 DM5790/07 Source: Wound | PA2-PAE 239 DM5790/07 Source: Wound | PA2-PAE 239 DM5790/07 Source: Wound |
| Test Concentration ug/ml | 4 hrs | 4 hrs | 4 hrs |
| 50.0 | 1.35 | 1.58 | 1.97 |
| 25.0 | 1.21 | 1.56 | 1.40 |
| 12.5 | 1.18 | 1.52 | 1.26 |
| 6.25 | 1.12 | 1.29 | 1.22 |
| 3.125 | 1.16 | 1.27 | 1.22 |

(B) Data for *P. aeruginosa* PAE249 DM15013

| Diluent for dilution of sample from 100 ug/ml to test concentration | USP Phosphate Buffer pH 7.2 | USP Phosphate Buffer pH 7.2 | USP Phosphate Buffer pH 7.2 |
|---|---|---|---|
| Type of Clinical *Pseudomonas aeruginosa* | PA4-PAE 249 DM15013 Source: Wound | PA4-PAE 249 DM15013 Source: Wound | PA4-PAE 249 DM15013 Source: Wound |
| Test Concentration ug/ml | 4 hrs | 4 hrs | 4 hrs |
| 50.0 | 5.08 | 4.57 | >4.99 |
| 25.0 | 4.69 | 4.34 | >4.99 |
| 12.5 | 3.96 | 4.19 | 4.60 |
| 6.25 | 3.13 | 2.41 | 3.18 |
| 3.125 | 2.12 | 2.00 | 1.71 |

TABLE 7

Antimicrobial activity of V2 dimer against clinical strains of *P. aeruginosa* (Log Reduction) isolated from urine at 35° C.

| Diluent for dilution of sample from 100 ug/ml to test concentration | USP Phosphate Buffer pH 7.2 | USP Phosphate Buffer pH 7.2 | USP Phosphate Buffer pH 7.2 |
|---|---|---|---|

TABLE 7-continued

Antimicrobial activity of V2 dimer against clinical strains of *P. aeruginosa* (Log Reduction) isolated from urine at 35° C.

| Type of Clinical *Pseudomonas aeruginosa* | PA3-PAE 240 DU14476/07 Source: Urine | PA3-PAE 240 DU14476/07 Source: Urine | PA3-PAE 240 DU14476/07 Source: Urine |
|---|---|---|---|
| Test Concentration ug/ml | 4 hrs | 4 hrs | 4 hrs |
| 50.0 | 2.08 | 1.88 | 1.72 |
| 25.0 | 1.58 | 1.52 | 1.56 |
| 12.5 | 1.21 | 1.52 | 1.42 |
| 6.25 | 1.25 | 1.52 | 1.28 |
| 3.125 | 1.15 | 1.52 | 1.13 |

TABLE 8

Antimicrobial activity of V2 dimer against *P. aeruginosa* (Log Reduction) isolated from the eye at 35° C. IN USP phosphate buffer (A) Data for *P. aeruginosa* 07DM02357

| Diluent for dilution of sample from 100 ug/ml to test concentration | USP Phosphate Buffer pH 7.2 | USP Phosphate Buffer pH 7.2 |
|---|---|---|
| Type of Clinical *Pseudomonas aeruginosa* | Ps-A 07DM02357 Source: Eye | Ps-A 07DM02357 Source: Eye |
| Test Concentration ug/ml | 4 hrs | 4 hrs |
| 50.0 | 2.41 | 5.53 |
| 25.0 | 1.76 | 3.66 |
| 12.5 | 1.75 | 3.17 |
| 6.25 | 1.60 | 2.35 |
| 3.125 | 1.37 | 1.94 |

(B) Data for *P. aeruginosa* 07DM023376

| Diluent for dilution of sample from 100 ug/ml to test concentration | USP Phosphate Buffer pH 7.2 | USP Phosphate Buffer pH 7.2 |
|---|---|---|
| Type of Clinical *Pseudomonas aeruginosa* | Ps-B 07DM023376 Source: Eye | Ps-B 07DM023376 Source: Eye |
| Test Concentration ug/ml | 4 hrs | 4 hrs |
| 50.0 | 2.39 | 2.25 |
| 25.0 | 1.81 | 2.18 |
| 12.5 | 1.76 | 2.15 |
| 6.25 | 1.38 | 1.88 |
| 3.125 | 1.07 | 1.16 |

(C) Data for *P. aeruginosa* 07DM023155

| Diluent for dilution of sample from 100 ug/ml to test concentration | USP Phosphate Buffer pH 7.2 | USP Phosphate Buffer pH 7.2 | USP Phosphate Buffer pH 7.2 |
|---|---|---|---|
| Type of Clinical *Pseudomonas aeruginosa* | Ps-C 07DM023155 Source: Eye | Ps-C 07DM023155 Source: Eye | Ps-C 07DM023155 Source: Eye |
| Test Concentration ug/ml | 4 hrs | 4 hrs | 4 hrs |
| 50.0 | 4.97 | 3.58 | 4.30 |
| 25.0 | 3.14 | 3.23 | 3.52 |
| 12.5 | 2.77 | 3.21 | 2.89 |
| 6.25 | 2.71 | 2.23 | 2.77 |
| 3.125 | 1.91 | 2.00 | 2.33 |

(D) Data for *P. aeruginosa* 07DM023104

| Diluent for dilution of sample from 100 ug/ml to test concentration | USP Phosphate Buffer pH 7.2 | USP Phosphate Buffer pH 7.2 |
|---|---|---|
| Type of Clinical *Pseudomonas aeruginosa* | Ps-D 07DM023104 Source: Eye | Ps-D 07DM023104 Source: Eye |
| Test Concentration ug/ml | 4 hrs | 4 hrs |
| 50.0 | 3.45 | 4.53 |
| 25.0 | 3.42 | 3.92 |
| 12.5 | 2.82 | 3.48 |
| 6.25 | 2.68 | 2.89 |
| 3.125 | 1.71 | 2.27 |

The antimicrobial activity of V2 dimer was also tested for clinical isolates from at physiological salt conditions using 10 mM phosphate buffer. V2 dimer also showed antimicrobial activity against clinical isolates from the eye in repeated experiments (Table 9A, 9B and 9C), the wound, sputum and urine in repeated experiments (Table 10A and B), suggesting that the V2 dimer can also be used against clinical isolates under physiological conditions.

TABLE 9

Antimicrobial activity of V2 dimer against *P. aeruginosa* (Log Reduction) isolated from the eye at 35° C. IN 10 mM potassium phosphate buffer at 35° C.

(A)

| Diluent for dilution of sample from 100 ug/ml to test concentration | 10 mM Sodium Phophate Buffer | 10 mM Phophate Buffer | 10 mM Sodium Phophate Buffer | 10 mM Sodium Phophate Buffer |
|---|---|---|---|---|
| Type of Clinical *Pseudomonas aeruginosa* | Ps-A 07DM02357 Source: Eye | Ps-B 07DM023376 Source: Eye | Ps-C 07DM023155 Source: Eye | Ps-D 07DM023104 Source: Eye |
| Test Concentration ug/ml | 4 hrs | 4 hrs | 4 hrs | 4 hrs |
| 50.0 | 2.92 | 2.23 | 3.47 | 3.77 |
| 25.0 | 2.05 | 1.87 | 3.14 | 2.09 |
| 12.5 | 1.04 | 1.29 | 1.60 | 1.47 |
| 6.25 | 0.97 | 1.18 | 1.62 | 1.04 |
| 3.125 | 0.56 | 0.45 | 0.94 | 0.61 |

(B)

| Diluent for dilution of sample from 100 ug/ml to test concentration | 10 mM Potassium Phophate Buffer | 10 mM Potassium Phophate Buffer | 10 mM Potassium Phophate Buffer | 10 mM Potassium Phophate Buffer |
|---|---|---|---|---|
| Type of Clinical *Pseudomonas aeruginosa* | Ps-A 07DM02357 Source: Eye | Ps-B 07DM023376 Source: Eye | Ps-C 07DM023155 Source: Eye | Ps-D 07DM023104 Source: Eye |
| Test Concentration ug/ml | 4 hrs | 4 hrs | 4 hrs | 4 hrs |
| 50.0 | 1.77 | 1.51 | 3.06 | 1.54 |
| 25.0 | 1.36 | 1.45 | 2.99 | 1.49 |
| 12.5 | 0.78 | 1.35 | 1.68 | 1.19 |
| 6.25 | 0.69 | 1.12 | 1.41 | 1.09 |
| 3.125 | 0.62 | 0.76 | 0.79 | 0.73 |

(C)

| Diluent for dilution of sample from 100 ug/ml to test concentration | 10 mM Potassium Phophate Buffer | 10 mM Potassium Phophate Buffer | 10 mM Potassium Phophate Buffer |
|---|---|---|---|
| Type of Clinical *Pseudomonas aeruginosa* | Ps-B 07DM023376 Source: Eye | Ps-C 07DM023155 Source: Eye | Ps-D 07DM023104 Source: Eye |
| Test Concentration ug/ml | 4 hrs | 4 hrs | 4 hrs |
| 50.0 | 2.28 | 2.62 | 1.39 |
| 25.0 | 1.90 | 2.33 | 0.97 |
| 12.5 | 0.95 | 1.70 | 0.46 |
| 6.25 | 1.01 | 1.14 | 0.13 |
| 3.125 | 0.64 | 0.09 | −0.54 |

TABLE 10

Antimicrobial activity of V2 dimer against clinical isolated *P. aeruginosa* (Log Reduction) isolated from wound, sputum and urine at 35° C. IN 10 mM postassium phosphate buffer (A)

| Diluent for dilution of sample from 100 ug/ml to test concentration | 10 mM Potassium Phophate Buffer | 10 mM Potassium Phophate Buffer | 10 mM Potassium Phophate Buffer | 10 mM Potassium Phophate Buffer |
|---|---|---|---|---|
| Type of Clinical *Pseudomonas aeruginosa* | PA1-PAE 230 DR4877/07 Source: Sputum | PA2-PAE 239 DM5790/07 Source: Wound | PA3-PAE 240 DU14476/07 Source: Urine | PA4-PAE 249 DM15013 Source: Wound |
| Test Concentration ug/ml | 4 hrs | 4 hrs | 4 hrs | 4 hrs |
| 50.0 | 2.54 | 1.21 | 1.28 | 3.01 |
| 25.0 | 2.03 | 0.78 | 1.11 | 2.02 |
| 12.5 | 1.14 | 0.58 | 0.72 | 1.30 |
| 6.25 | 0.66 | 0.40 | 0.61 | 0.97 |
| 3.125 | 0.21 | 0.06 | 0.29 | 0.26 |

(B)

| Diluent for dilution of sample from 100 ug/ml to test concentration | 10 mM Potassium Phophate Buffer | 10 mM Potassium Phophate Buffer | 10 mM Potassium Phophate Buffer | 10 mM Potassium Phophate Buffer |
|---|---|---|---|---|
| Type of Clinical *Pseudomonas aeruginosa* | PA1-PAE 230 DR4877/07 Source: Sputum | PA1-PAE 230 DR4877/07 Source: Sputum | PA2-PAE 239 DM5790/07 Source: Wound | PA2-PAE 239 DM5790/07 Source: Wound |
| Test Concentration ug/ml | 4 hrs | 4 hrs | 4 hrs | 4 hrs |
| 50.0 | 2.54 | 2.36 | 1.21 | 1.59 |
| 25.0 | 2.03 | 1.97 | 0.78 | 1.27 |
| 12.5 | 1.14 | 1.26 | 0.58 | 0.77 |
| 6.25 | 0.66 | 0.97 | 0.40 | 0.62 |
| 3.125 | 0.21 | 0.64 | 0.06 | 0.49 |

Example 6

Comparison of Antimicrobial Activity of V2 Dimer and Gentamicin

A comparison of the antimicrobial activity of V2 dimer and gentamicin was made against clinical isolates of *Pseudomonas aeruginosa*.

In the first study, both V2 dimer and gentamicn were tested against clinical isolates from wound and sputum and compared (See Table 5). The study showed that for the wound isolate, V2 dimer has comparable activity to gentamicin. For the sputum isolate, V2 dimer showed higher antimicrobial activity.

TABLE 11

Comparision of the antimicrobial activity (Log Reduction) V2 dimer with gentamicin against clinical *P. aeruginosa* isolates from sputum and wound at 35° C.:

| | V2-dimer | V2-dimer | Gentamicin | Gentamicin |
|---|---|---|---|---|
| Diluent for dilution of sample from 100 ug/ml to test concentration | USP Phosphate Buffer | USP Phosphate Buffer | USP Phosphate Buffer | USP Phosphate Buffer |
| Type of Clinical *Pseudomonas aeruginosa* | PA1-PAE 230 DR4877/07 Source: Sputum | PA2-PAE 239 DM5790/07 Source: Wound | PA1-PAE 230 DR4877/07 Source: Sputum | PA2-PAE 239 DM5790/07 Source: Wound |
| Test Concentration ug/ml | 4 hrs | 4 hrs | 4 hrs | 4 hrs |
| 50.0 | >4.79 | 2.52 | 0.39 | 3.31 |
| 25.0 | >4.79 | 2.69 | 0.54 | 3.04 |
| 12.5 | >4.79 | 2.36 | 0.65 | 3.03 |
| 6.25 | >4.79 | 2.28 | 0.35 | 3.07 |
| 3.125 | >4.79 | 2.04 | 0.22 | 3.02 |

In a second study, the antimicrobial activity of both V2 dimer and gentamicn were tested against clinical isolates from urine and sputum and compared (See Table 6). The V2 dimer also showed comparable activity to gentamicin against these two isolates.

TABLE 12

Comparison of the antimicrobial activity (Log Reduction) V2 dimer with gentamicin against clinical *P. aeruginosa* isolates from urine and wound at 35° C.:

| | V2-dimer | V2-dimer | Gentamicin | Gentamicin |
|---|---|---|---|---|
| Diluent for dilution of sample from 100 ug/ml to test concentration | USP Phosphate Buffer pH 7.2 | USP Phosphate Buffer pH 7.2 | USP Phosphate Buffer pH 7.2 | USP Phosphate Buffer pH 7.2 |
| Type of Clinical *Pseudomonas aeruginosa* | PA3-PAE 240 DU14476/07 Source: Urine | PA4-PAE 249 DM15013 Source: Wound | PA3-PAE 240 DU14476/07 Source: Urine | PA4-PAE 249 DM15013 Source: Wound |
| Test Concentration ug/ml | 4 hrs | 4 hrs | 4 hrs | 4 hrs |
| 50.0 | 1.81 | 5.19 | 4.57 | 2.63 |
| 25.0 | 1.51 | 3.86 | 4.18 | 2.60 |
| 12.5 | 1.40 | 3.75 | 3.88 | 2.50 |
| 6.25 | 1.22 | 3.73 | 3.76 | 2.41 |
| 3.125 | 1.11 | 3.77 | 3.66 | 2.28 |

In a third study, the antimicrobial activity of both V2 dimer and gentamicin were tested against clinical isolates from the eye (See Table 13). This study shows that V2 dimer and gentamicin have comparable activity against *P. aeruginosa* isolates from the eye.

TABLE 13

Comparision of the antimicrobial activity (Log Reduction) V2 dimer with gentamicin against clinical *P. aeruginosa* isolates from urine and wound at 35° C.:

| | V2-dimer | V2-dimer | Gentamicin | Gentamicin |
|---|---|---|---|---|
| Diluent for dilution of sample from 100 ug/ml to test concentration | USP Phosphate Buffer pH 7.2 | USP Phosphate Buffer pH 7.2 | USP Phosphate Buffer pH 7.2 | USP Phosphate Buffer pH 7.2 |
| Type of Clinical *Pseudomonas aeruginosa* | Ps-C 07DM023155 Source: Eye | Ps-D 07DM023104 Source: Eye | Ps-C 07DM023155 Source: Eye | Ps-D 07DM023104 Source: Eye |
| Test Concentration ug/ml | 4 hrs | 4 hrs | 4 hrs | 4 hrs |
| 50.0 | 4.31 | >4.33 | >4.61 | >4.33 |
| 25.0 | 3.80 | >4.33 | >4.61 | >4.33 |
| 12.5 | 3.17 | 4.02 | >4.61 | >4.33 |
| 6.25 | 3.11 | 3.75 | >4.61 | >4.33 |
| 3.125 | 2.74 | 3.35 | >4.61 | >4.33 |

Taken together, the above studies suggest that V2 dimer and gentamicin have comparable antimicrobial activity and the V2 dimer may be used with an efficacy equivalent to gentamicin against microorganisms.

Example 7

Antimicrobial Activity of V2 Dimer Against Other Organisms (A) *Candida albicans* ATCC 10231

The antimicrobial activity of V2 dimer against *Candida albicans* ATCC 10231 was tested. *C. albicans* at $7.2 \times 10^5$ CFU in USP phosphate buffer were mixed with different concentrations of V2 dimer and incubated for 4 hours at 35° C. The results show that V2 dimer at 50 ug, 25 ug and 12.5 ug/ml achieved 3.6 to 4 log reductions against *C. albicans* ATCC 10231. (Table 14)

TABLE 14

Antimicrobial Activity against *Candida albicans* ATCC 10231 (Log Reduction) at 35° C.

| Test Concentration of V2 dimer (μg/ml) | Time (hours) | Mean Log reduction |
|---|---|---|
| 50 | 4 | 3.94 |
| 25 | 4 | 4.01 |
| 12.5 | 4 | 3.62 |
| 6.25 | 4 | 2.30 |
| 3.125 | 4 | 0.71 |

(B) *Bacillus cereus* ATCC 11778

The antimicrobial activity of V2 dimer against *Bacillus cereus* ATCC 11778 was tested. V2 dimer showed antimicrobial activity against *B. cereus* (Table 15)

TABLE 15

Antimicrobial Activity against *Bacillus cereus* ATCC 11778 (Log Reduction) at 35° C.

| Diluent for dilution of sample from 100 ug/ml to test concentration | USP Phosphate Buffer pH 7.2 | USP Phosphate Buffer pH 7.2 |
|---|---|---|
| Test Concentration ug/ml | 4 hours | 4 hours |
| 50.0 | 2.29 | 1.70 |
| 25.0 | 2.76 | 2.04 |
| 12.5 | 2.75 | 1.32 |
| 6.25 | 0.86 | 1.26 |

(C) Clinical *Escherichia coli* DB0016027R

In addition, the V2 dimer was able to produce reductions against the multiple antibiotic resistant strain of *E. coli* DB0016027R (clinically isolated from blood) which has an antibiogram profile of resistance to gentamicin, amplicillin and other antibiotics.

TABLE 16

Antimicrobial Activity against *E. coli* DB0016027R (Log Reduction) at 35° C.

| Diluent for dilution of sample from 100 ug/ml to test concentration | USP Phosphate Buffer pH 7.2 |
|---|---|
| Test Concentration ug/ml | 4 hours |
| 50.0 | 2.83 |
| 25.0 | 2.52 |
| 12.5 | 2.68 |
| 6.25 | 2.45 |
| 3.125 | 2.60 |

V2 dimer's antimicrobial property against *C. albicans* and other bacteria suggests that it may be an effective broad spectrum antimicrobial. Further, V2 dimer's efficacy against a multiple antibiotic resistant strain of *E. coli* suggests that it may be an effective therapeutic agent against where other antibiotics cannot be used.

Example 8

Cytotoxicity of V2 Dimer

The cytotoxicity of V2 dimer were tested against human conjunctival cells according to the method described in WO 2007/126392 and compared with native hBD3. FIG. 4 shows that V2 dimer has reduced cytotoxicity to human conjunctival cells in comparison with wildtype hBD3. Wildtype hBD3 was cytotoxic at concentrations of about 15 μg/ml, however, the V2 dimer was not cytotoxic at concentrations of 100 μg/ml. The cytotoxicity profile of the V2 dimer was comparable to that of the monomer peptides from WO 2007/126392

The reduced cytotoxicity of V2 dimer to human conjunctival cells and the high antimicrobial activity of the V2 dimer suggest that this dimer could be used in a host for treating microbial infections and/or reducing the growth of microorganism in the host. Other dimers of the peptides from WO 2007/126392 are similarly expected to also show high antimicrobial activity and low cytotoxicity.

Example 9

Minimum Inhibitory Concentration (MIC) Determination by Broth Macrodilution Technique MICs was determined by broth macrodilution method modified from that described by the National Committee for Clinical Laboratory Standards (NCCL). The Mueller Hinton Broth (MHB) at 1/6 strength and without addition of $Ca^{2+}$ and $Mg^{2+}$ was used for dilution. Serial twofold dilutions of V2 dimer solution ws prepared in MHB (1/6 strength) in test tubes. 1 ml of inoculum of test organisms in MHB (1/6 strength) was added to 1 ml of each dilution of V2 dimer to yield as final concentration of $10^4$ to $10^5$ colony forming units/ml in each test tube. The tubes were incubated at 35° C. for 16 to 20 hours. A positive control containing only the borth and organism, and a negative control tube containing only the broth were also incubated in parallel to the test samples. The above was repeated for each different test organism in separate experiments. The MIC of V2 dimer peptide for each clinical isolate or reference organism was read as the lowest concentration of peptide that inhibited visible growth of the test organism.

The MIC was also determined for other peptides and compared to gentamicin. The MIC results are shown in Tables 17-20.

TABLE 17

MIC (ug/ml) results of V2-dimer, Y2-dimer, W2-dimer and gentamicin against different strains of Gram-negative bacteria *Pseudomonas aeruginosa* and *Escherichia coli*

| Test Organism | V2-dimer | Y2-dimer | W2-dimer | V2-tetramer | Gentamicin |
|---|---|---|---|---|---|
| *Pseudomonas aeruginosa* ATCC 27853 | 12.5 | | | | |
| Clinical *Pseudomonas aeruginosa* DM 023104 Source: Eye | 12.5 | 12.5 | 12.5 | 6.25 | |
| Clinical *Pseudomonas aeruginosa* DM 023155 Source: Eye | 12.5 | 25 | 12.5 | 6.25 | |
| Clinical *Pseudomonas aeruginosa* 07DM 023257 Source: Eye | 12.5 | 12.5 | 12.5 | 12.5 | |
| Clinical *Pseudomonas aeruginosa* 07DM023376 Source: Eye | 12.5 | 25 | 25 | 6.25 | |
| Clinical *Pseudomonas aeruginosa* PAE 230 DR4877/07 Source: Sputum | 12.5 | 12.5 | 12.5 | 12.5 | 400 |
| Clinical *Pseudomonas aeruginosa* PAE 239 DM5790/07 Source: Wound | 12.5 | 12.5 | 12.5 | 12.5 | 25 |
| Clinical *Pseudomonas aeruginosa* PAE 240 DU14476/07 Source: Urine | 6.25 | 6.25 | 12.5 | 6.25 | |
| Clinical *Pseudomonas aeruginosa* PAE 249 DM15013 Source: Wound | 6.25 | 12.5 | 6.25 | 6.25 | |
| *Escherichia coli* ATCC25922 | 12.5 | 12.5 | 25 | 12.5 | |
| Clinical *Escherichia coli* DB16027 Source: Blood | 6.25 | 6.25 | 12.5 | 6.25 | 0.78 |
| Clinical *Escherichia coli* DU46381R Source: Urine | 6.25 | 12.5 | 6.25 | 6.25 | |

TABLE 18

MIC (ug/ml) results of V2-dimer, Y2-dimer, W2-dimer and Gentamicin against different strains of Gram-positive bacteria *Staphylococcus ureus, Bacillus cereus* and fungi *Candida albicans, Fusarium solani*

| Test Organism | V2-dimer | Y2-dimer | W2-dimer | V2-tetramer | Gentamicin |
|---|---|---|---|---|---|
| Methicillin-resistant *staphylococcus aureus* (MRSA) DM09808R Source: Eye | 12.5 | | | | 12.5 |
| Clinical *Staphylococcus aureus* DM4001 Source: Eye | 12.5 | 12.5 | 12.5 | 12.5 | |
| *Bacillus cereus* ATCC 11778 | 12.5 | | | | |
| *Candida albicans* ATCC10231 | 12.5 | 25 | 12.5 | 12.5 | |
| Clinical *Cadida albicans* DF2672R Source: Urine | 12.5 | 12.5 | 12.5 | 12.5 | |
| *Fusarium solani* ATCC 36031 | 25 | 12.5 | 12.5 | 3.125 | |

TABLE 19

MIC (ug/ml) results of several C-terminus monomers against different strains of Gram-negative bacteria *Pseudomonas aeruginosa* and *Escherichia coli*

| Test Organism | Y2-8AA | V2-8AA | W2-8AA | V4 monomer | Y4 monomer |
|---|---|---|---|---|---|
| *Pseudomonas aeruginosa* ATCC 27853 | | | | | |
| Clinical *Pseudomonas aeruginosa* DM 023104 Source: Eye | >50 | >50 | 25 | >50 | 50 |
| Clinical *Pseudomonas aeruginosa* DM 023155 Source: Eye | >50 | >50 | 50 | >50 | 25 |
| Clinical *Pseudomonas aeruginosa* 07DM 023257 Source: Eye | >50 | >50 | >50 | >50 | >50 |
| Clinical *Pseudomonas aeruginosa* 07DM023376 Source: Eye | 50 | >50 | 25 | >50 | >50 |
| Clinical *Pseudomonas aeruginosa* PAE 230 DR4877/07 Source: Sputum | >50 | >50 | >50 | >50 | >50 |
| Clinical *Pseudomonas aeruginosa* PAE 239 DM5790/07 Source: Wound | >50 | >50 | >50 | >50 | 50 |
| Clinical *Pseudomonas aeruginosa* PAE 240 DU14476/07 Source: Urine | 6.25 | 25 | 12.5 | >50 | 25 |
| Clinical *Pseudomonas aeruginosa* PAE 249 DM15013 Source: Wound | | >50 | >50 | 50 | >50 | 50 |
| *Escherichia coli* ATCC25922 | | 25 | >50 | 12.5 | >50 | 12.5 |
| Clinical *Escherichia coli* DB16027 Source: Blood | | 25 | >50 | 6.25 | >50 | 6.25 |
| Clinical *Escherichia coli* DU46381R Source: Urine | | 25 | 50 | 6.25 | >50 | 12.5 |

TABLE 20

MIC (ug/ml) results of several C-terminus monomers against different strains of Gram-positive bacteria *Staphylococcus ureus*, *Bacillus cereus* and fungi *Candida albicans*, *Fusarium solani*

| Test Organism | Y2-8AA | V2-8AA | W2-8AA | V4 monomer | Y4 monomer |
|---|---|---|---|---|---|
| Methicillin-resistant *staphylococcus aureus* (MRSA) DM09808R Source: Eye | | | | | |
| Clinical *Staphylococcus aureus* DM4001 Source: Eye | >50 | >50 | 12.5 | >50 | 12.5 |
| *Bacillus cereus* ATCC 11778 | | | | | |
| *Candida albicans* ATCC10231 | 25 | >50 | 12.5 | 25 | 12.5 |
| Clinical *Cadida albicans* DF2672R Source: Urine | 50 | >50 | 12.5 | >50 | 25 |
| *Fusarium solani* ATCC 36031 | 50 | >100 | 25 | >100 | 12.5 |

REFERENCES

Campopiano D. J., Clarke, D. J., Polfer, N. C., Barran, P. E., Langley, R. J., Gvan. J. R., Maxwell, A., and Donn, J. R. (2004) Structure-activity relationships in defensin dimers: a novel link between beta-defensin tertiary structure and antimicrobial activity. J. Biol. Chem. 279(47):48671-29.

Hoover D. M., Rajashankar K. R., Blumenthal R., Puri A., Oppenheim J. J., Chertov O. and Lubkowski J., (2000) The structure of human beta-defensin-2 shows evidence of higher order oligomerization. J. Biol. Chem. 275(42):32911-8.

Hoover D, M., Chertov O. and Lubkowski J., (2001) The structure of human beta-defensin-1: insights into structural properties of beta-defensins. J. Biol. Chem. 276(42):39021-6.

Krajewski K., Marchand C., Long, Y-Q., Pommier, Y. and Roller, P. P. (2004) Synthesis and HIV-1 integrase inhibitory activity of dimeric and tetrameric analogs of indolicin Bioorganic and Medicinal Chemistry Letters 14: 5595-5598.

National Committee for Clinical Laboratory Standards (1987) Methods for determining bactericidal activity of antimicrobial agents by National Committee for Clinical Laboratory Standards (Villanova, Pa.).

Schibli D. J., Hunter H. N. Aseyev V., Starner T, D. Wiencek J. M., McCray Jr P. B., Tack B. F. and Vogel H. J. (2002) The solution structures of the human beta-defensins lead to a better understanding of the potent bactericidal activity of HBD3 against *Staphylococcus aureus* J. Biol. Chem. 276 (42):8279-8289

WO 2007/126392

The invention claimed is:

1. An isolated multimer of defensin peptides of formula $(U)_n B_m Z_j$, wherein U is a peptide comprising any one of SEQ ID NOS:3-53, 57, or 58, wherein n≥2, m≥1, and j≥0, wherein each B comprises at least one amino acid having at least two amine groups, wherein Z comprises any amino acid, and wherein the multimer is branched at the terminal $B_m Z_j$ residues.

2. The isolated multimer according to claim 1, wherein the peptide U has a charge of +1 to +11.

3. The isolated multimer according to claim 1, wherein each B comprises lysine, ornithine or arginine.

4. The isolated multimer according to claim 1, wherein m=n−1, j=1, B=Z=K, the multimer has the formula $(U)_n K_{n-1} K$, and U comprises any one of SEQ ID NOs: 36 to 44.

5. A method of preparing the multimer according to claim 1 comprising
(i) providing at least one solid phase;
(ii) coupling at least a first amino acid Z to the solid phase;
(iii) linking at least one protected amino acid residue B to the coupled Z;
(iv) removing the protecting group(s) from the linked B amino acid residue(s)
(v) providing additional chain extension by linking protected amino acid residues, according to the sequence of the peptide U from the C-terminus to the N-terminus, wherein after each linking, the protecting groups are removed for the next linking;
(vi) terminating the linking of amino acid residues depending on the number of residues to be added; and
(vii) optionally, releasing the multimer from the solid phase.

6. The method according to claim 5, further comprising, after step (iv):
(iv)(a) linking further protected B residues to the linked B residue(s);
(iv)(b) removing the protecting group(s) from the B residues from (iv)(a);
(iv)(c) repeating step (iv)(a) and (iv)(b), or
(iv)(d) proceeding to step (v) and (vi).

7. The method according to claim 5, wherein each B comprises lysine, arginine or ornithine.

8. The method according to claim 5, wherein the peptide U comprises SEQ ID NO: 3 or any one of SEQ ID Nos: 36 to 44.

9. A contact lens solution for coating a device comprising the multimer according to claim 1.

10. A method of inhibiting and/or reducing the growth of at least one microorganism comprising contacting the microorganism with at least one multimer according to claim 1.

11. A method of treating at least one microbial infection comprising administering to a subject at least one multimer according to claim 1.

12. A method of inhibiting and/or reducing the growth of at least one microorganism in a subject comprising administering to the subject at least one multimer according to claim 1.

13. A method of preparing a peptide trimer of formula $(U^1)_2 B U^1 Z$, wherein $U^1$ comprises any one of SEQ ID NOS: 3-53, 57, or 58, B comprises an amino acid comprising at least two amine groups and Z comprises any amino acid, the method comprising the steps of:
(i) providing at least one solid phase;
(ii) coupling at least a first amino acid Z to the solid phase; and
(iii) providing chain extension of peptide $U^1$ to Z;
(iv) linking a protected amino acid B to an amino acid of peptide $U^1$;
(v) removing the protecting groups from the linked amino acid B; and
(vi) providing for chain extension of two peptides $U^1$ to the amino acid B.

14. An isolated peptide trimer of formula $(U^1)_2 B U^1 Z$; wherein $U^1$ comprises any one of SEQ ID NOS: 3-53, 57, or 58; B comprises an amino acid comprising at least two amine groups and Z comprises any amino acid.

15. The isolated multimer according to claim 1, wherein B=Z=K and the multimer has the formula $(U)_n K_m K_j$.

16. The isolated multimer according to claim 1, wherein B=Z=K, m=n−1, j=1 and the multimer has the formula $(U)_n K_{n-1} K_1$.

17. An eye drop solution for coating a device comprising the multimer according to claim 1.

18. An antimicrobial pharmaceutical composition for coating a device comprising the multimer according to claim 1.

* * * * *